(12) United States Patent
Liu et al.

(10) Patent No.: US 11,364,209 B2
(45) Date of Patent: Jun. 21, 2022

(54) METHODS AND COMPOSITIONS FOR TREATING ATOPIC DERMATITIS

(71) Applicant: Golden Biotechnology Corporation, Jersey City, NJ (US)

(72) Inventors: Sheng-Yung Liu, New Taipei (TW); Chih-Ming Chen, New Taipei (TW)

(73) Assignee: Golden Biotechnology Corporation, Jersey City, NJ (US)

( * ) Notice: Subject to any disclaimer, the term of this patent is extended or adjusted under 35 U.S.C. 154(b) by 0 days.

(21) Appl. No.: 16/349,155

(22) PCT Filed: Nov. 17, 2017

(86) PCT No.: PCT/US2017/062121
§ 371 (c)(1),
(2) Date: May 10, 2019

(87) PCT Pub. No.: WO2018/094122
PCT Pub. Date: May 24, 2018

(65) Prior Publication Data
US 2019/0282515 A1 Sep. 19, 2019

Related U.S. Application Data

(60) Provisional application No. 62/423,783, filed on Nov. 18, 2016.

(51) Int. Cl.
| | | |
|---|---|---|
| *A61K 31/122* | (2006.01) | |
| *A61P 17/00* | (2006.01) | |
| *A61K 9/00* | (2006.01) | |
| *A61K 36/07* | (2006.01) | |
| *C07C 403/04* | (2006.01) | |
| *C07C 403/18* | (2006.01) | |
| *A61K 9/48* | (2006.01) | |
| *C07C 403/20* | (2006.01) | |
| *A61P 29/00* | (2006.01) | |
| *C07C 403/02* | (2006.01) | |
| *C07C 403/16* | (2006.01) | |
| *C07C 403/08* | (2006.01) | |
| *C07C 403/14* | (2006.01) | |

(52) U.S. Cl.
CPC ............ *A61K 31/122* (2013.01); *A61K 9/006* (2013.01); *A61K 9/0019* (2013.01); *A61K 9/0053* (2013.01); *A61K 9/0078* (2013.01); *A61K 9/4858* (2013.01); *A61K 9/4866* (2013.01); *A61K 36/07* (2013.01); *A61P 17/00* (2018.01); *A61P 29/00* (2018.01); *C07C 403/02* (2013.01); *C07C 403/04* (2013.01); *C07C 403/08* (2013.01); *C07C 403/14* (2013.01); *C07C 403/16* (2013.01); *C07C 403/18* (2013.01); *C07C 403/20* (2013.01); *C07C 2601/16* (2017.05)

(58) Field of Classification Search
CPC .................................................... A61K 31/122
See application file for complete search history.

(56) References Cited

U.S. PATENT DOCUMENTS

| 5,811,455 | A | 9/1998 | Christensen, IV et al. |
| 7,501,454 | B2 * | 3/2009 | Liu ......................... A61P 37/06 514/690 |
| 2008/0234225 | A1 * | 9/2008 | Lezdey ................ A61K 31/198 514/58 |
| 2008/0312334 | A1 | 12/2008 | Liu et al. |
| 2014/0286989 | A1 | 9/2014 | Chang et al. |
| 2015/0336918 | A1 | 11/2015 | Chang et al. |
| 2016/0185703 | A1 | 6/2016 | Liu et al. |

FOREIGN PATENT DOCUMENTS

WO WO 2016/011130 A1 1/2016

* cited by examiner

Primary Examiner — Yong S. Chong

(57) ABSTRACT

The present invention provides methods and compositions for treating atopic dermatitis by cyclohexenone compounds.

8 Claims, 17 Drawing Sheets

FIG. 2A-E
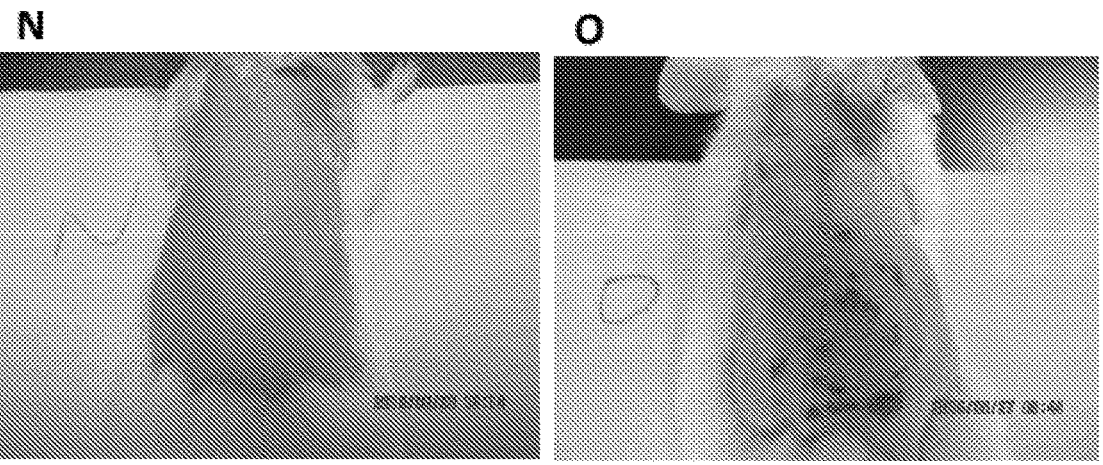
2A  2B
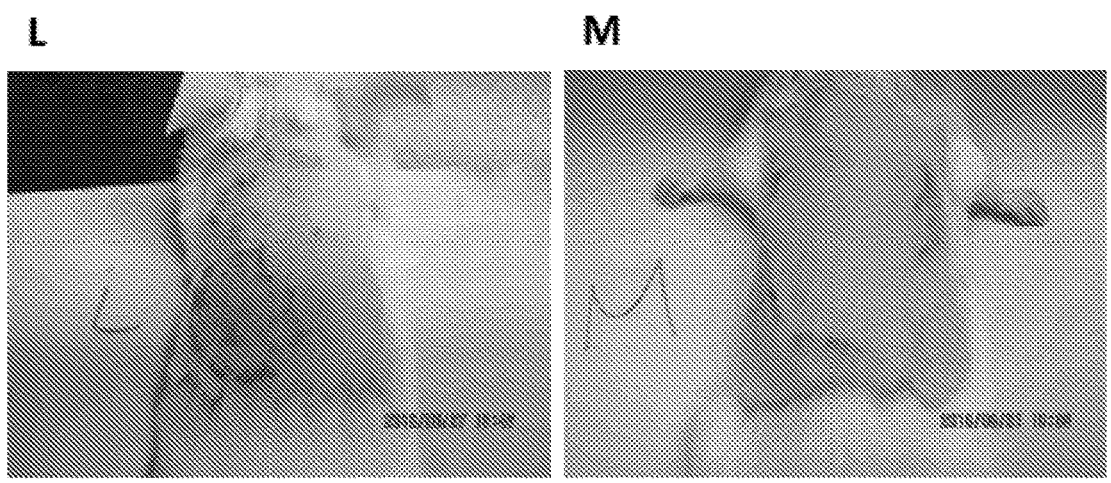
2C  2D
2E

FIG. 3A-C
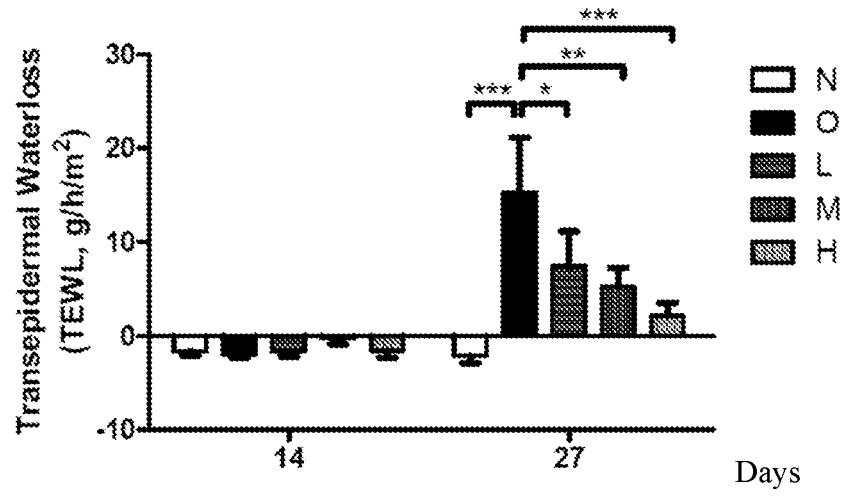
3A
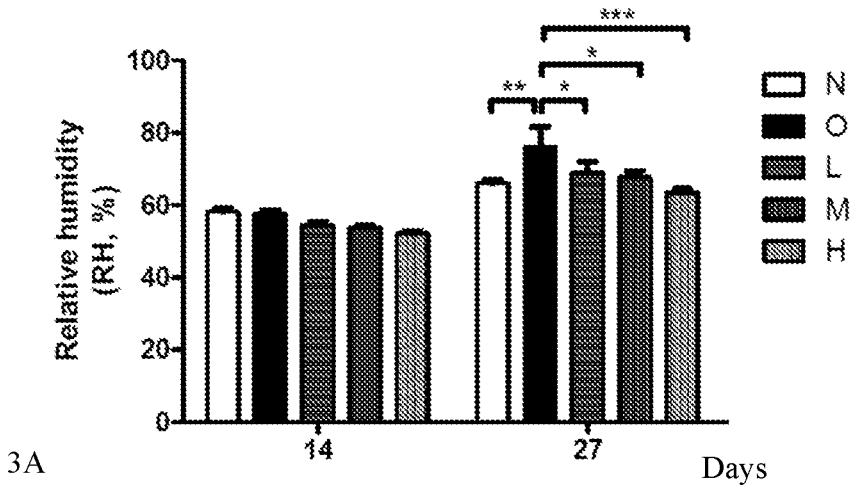
3B
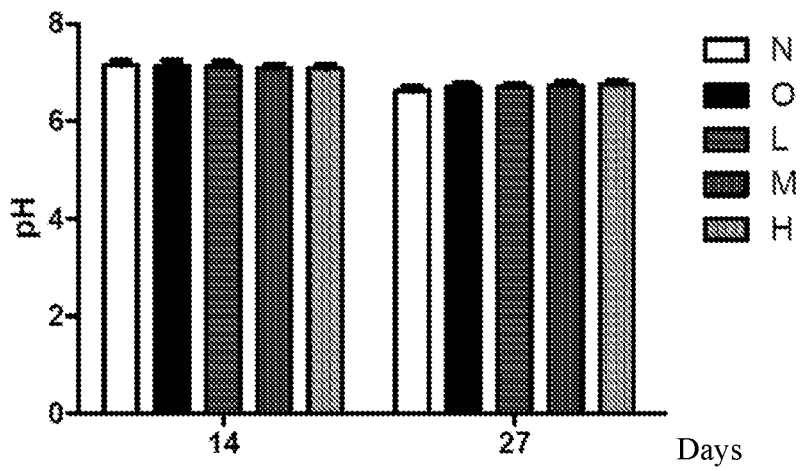
3C

FIG. 4A-E
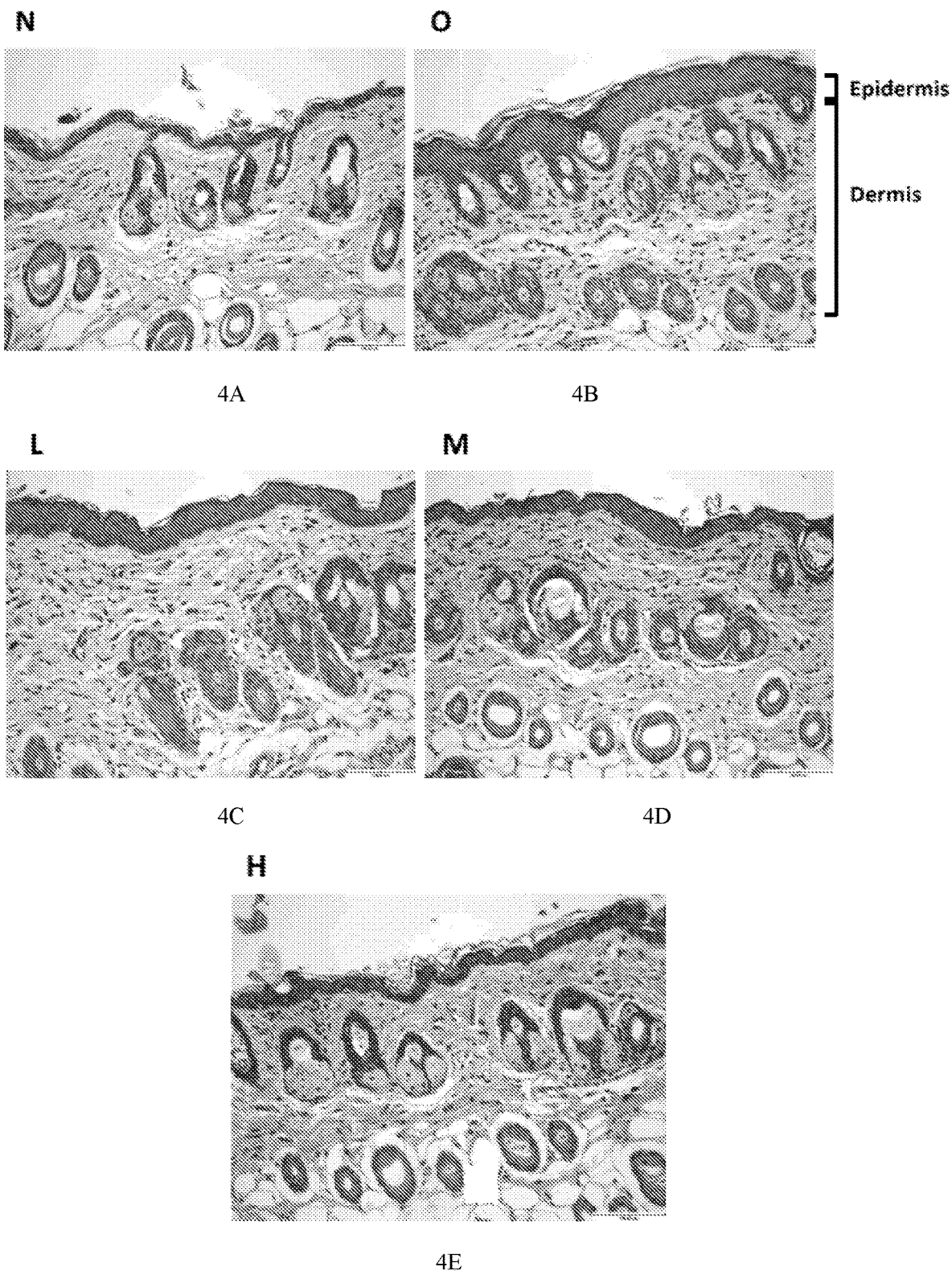

FIG. 4F/G
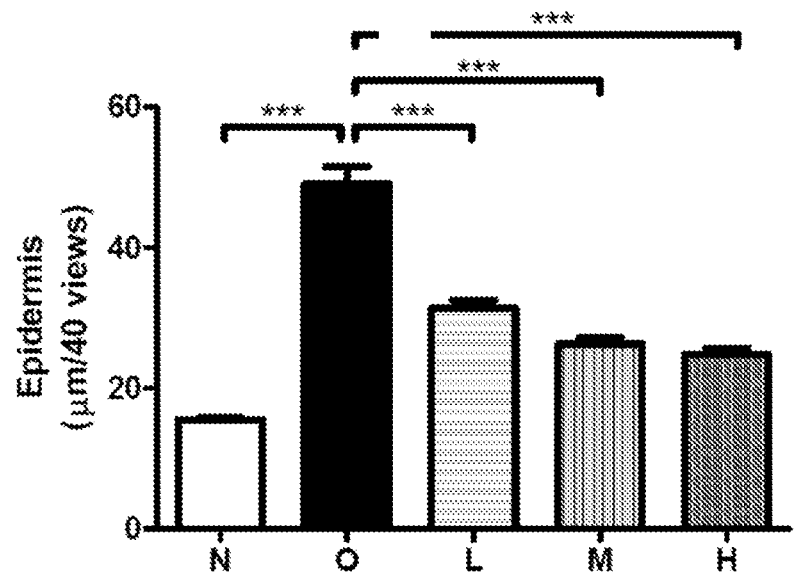
4F
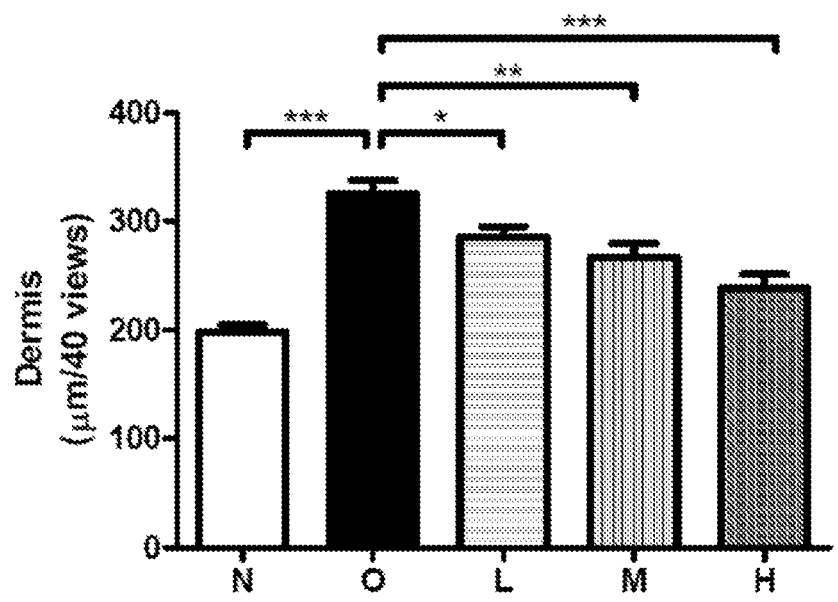
4G

FIG. 5A-D
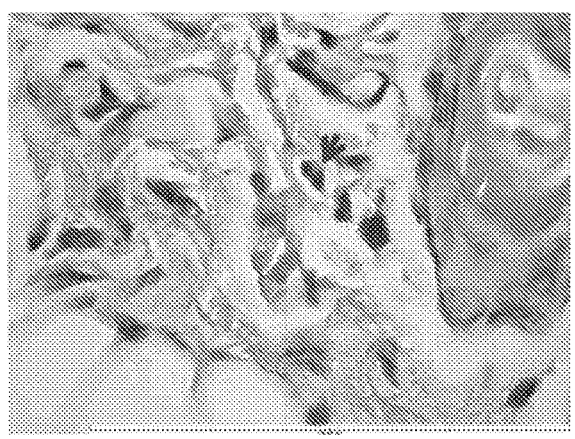
5A
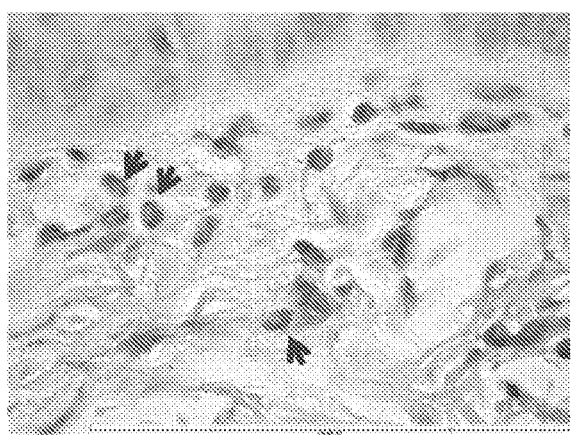
5B
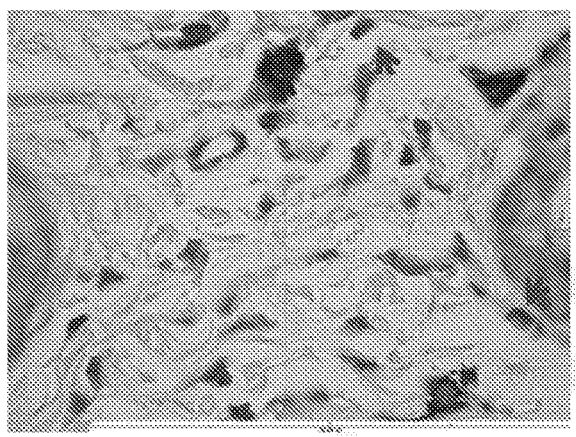
5C
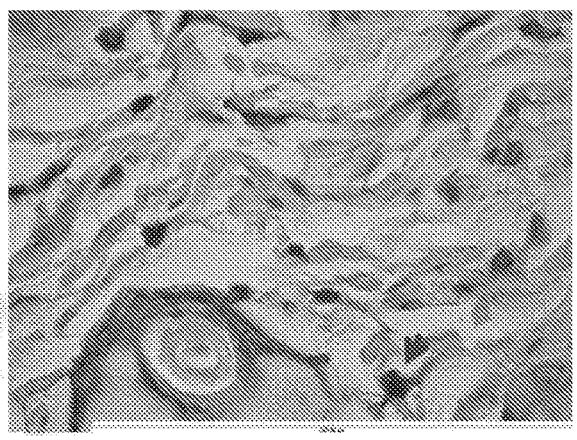
5D

FIG. 5E/F
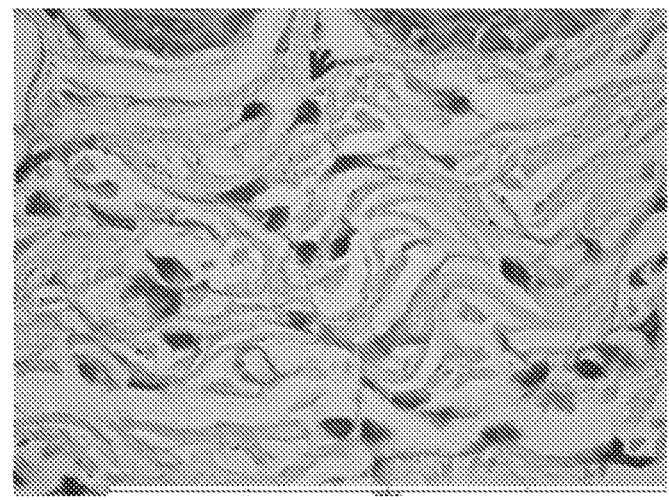
5E
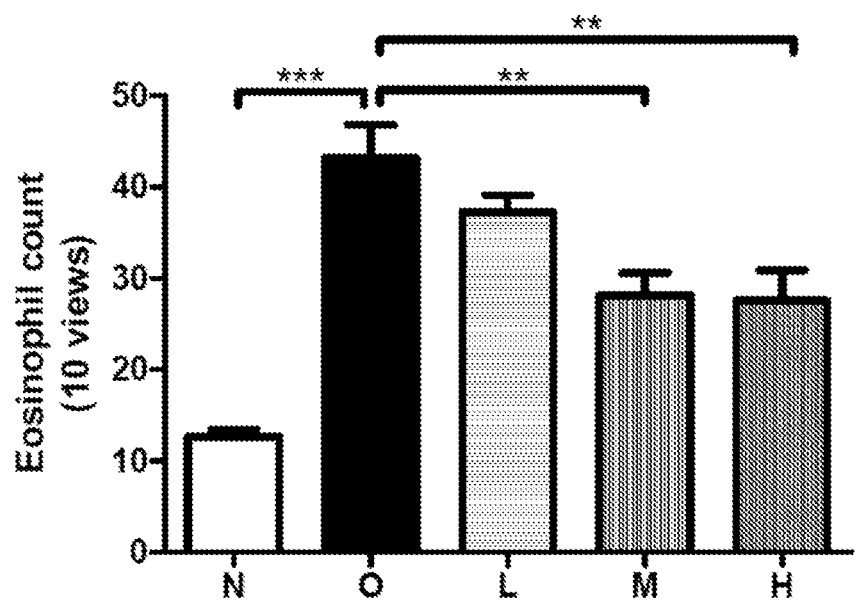
5F

FIG. 6A-D
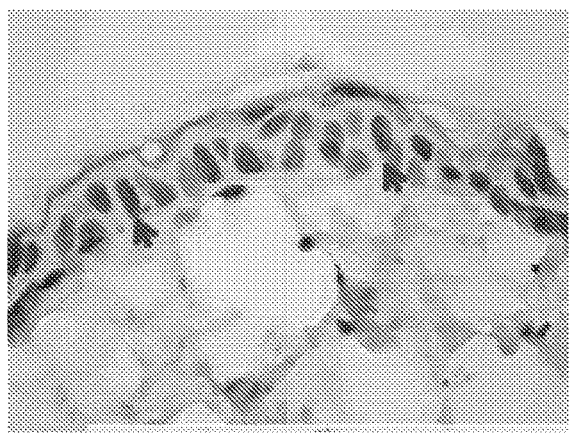
6A
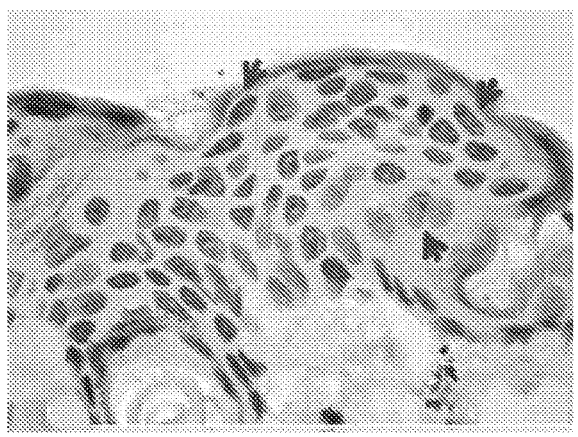
6B
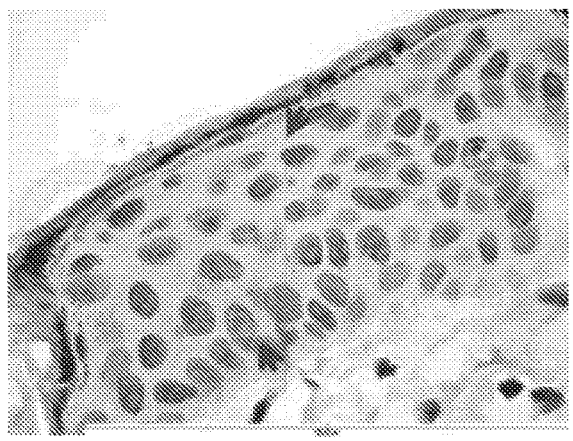
6C
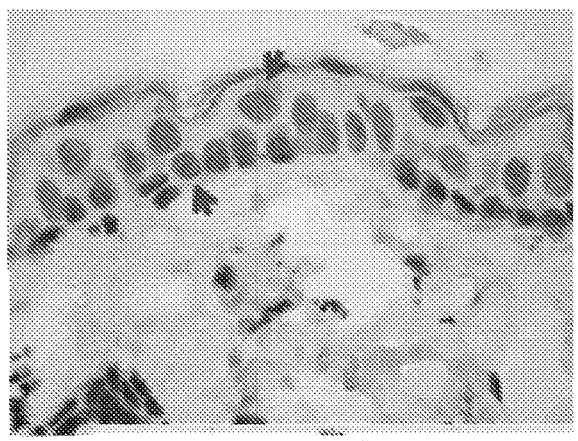
6D

FIG. 6E/F
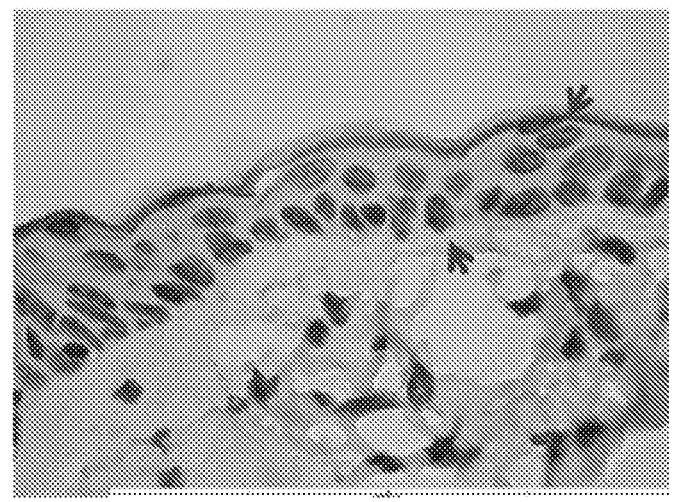
6E
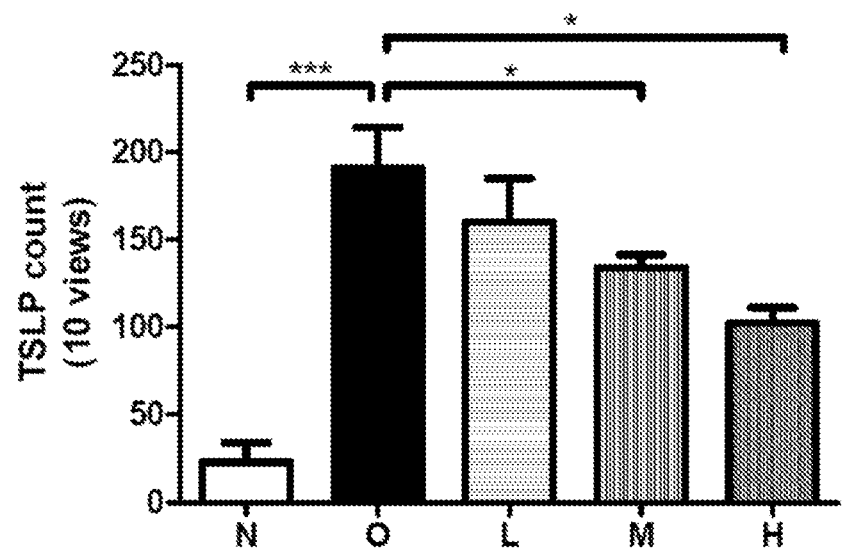
6F

FIG. 7A-D
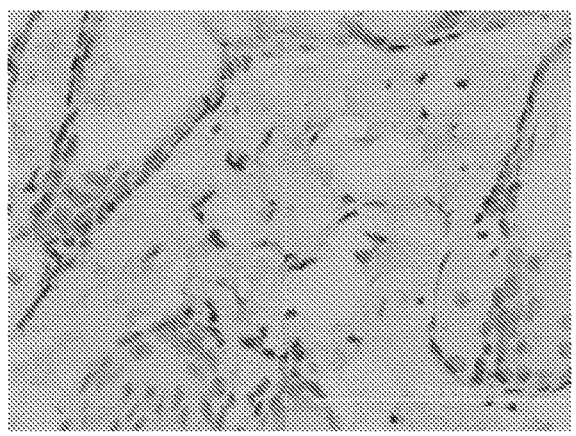
7A
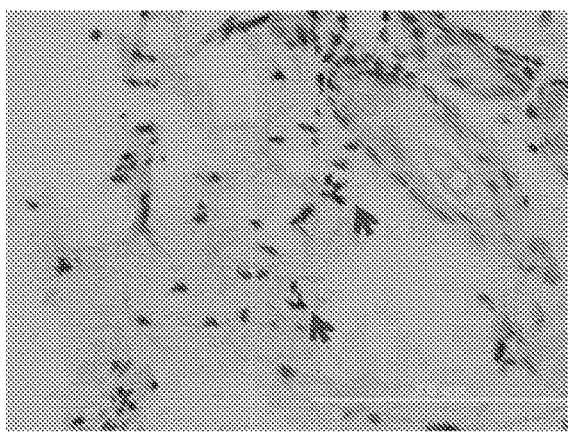
7B
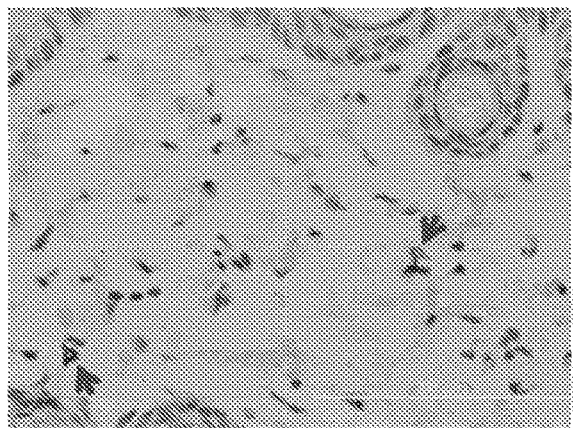
7C
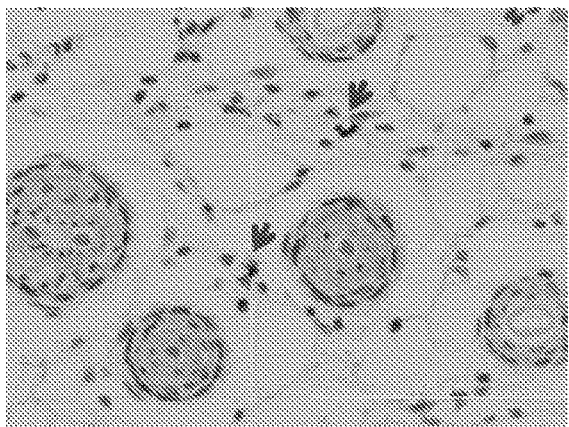
7D

FIG. 7E/F
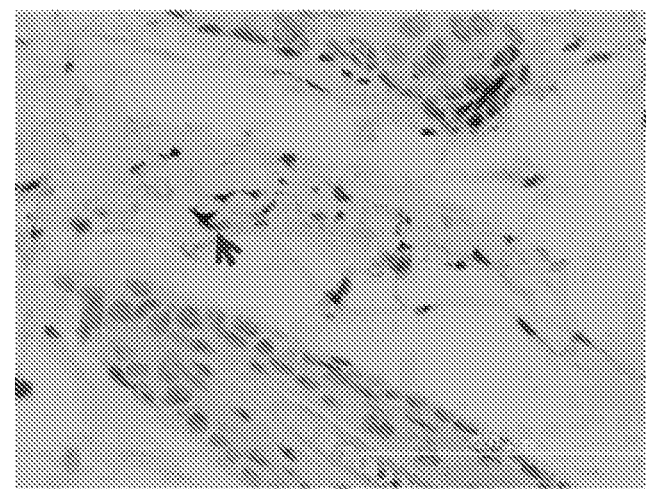
7E
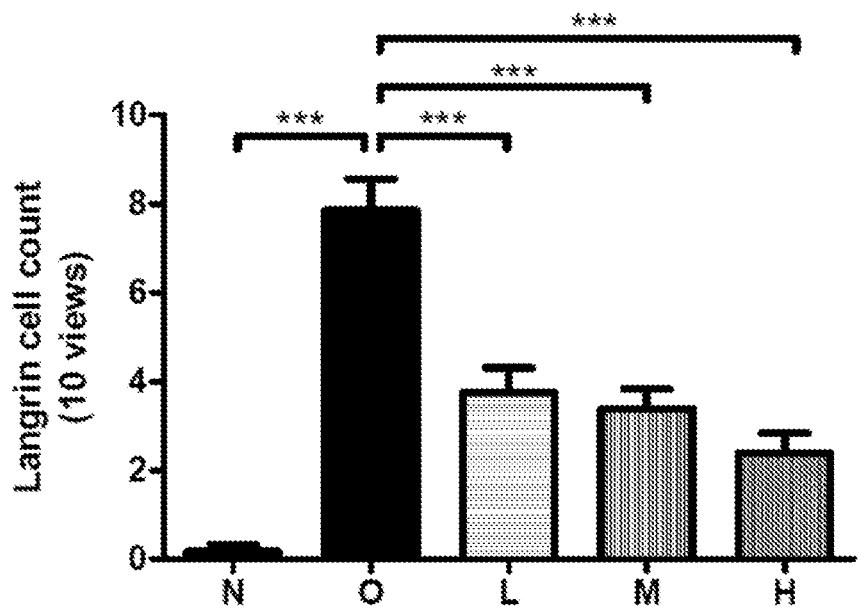
7F

FIG. 8A/B
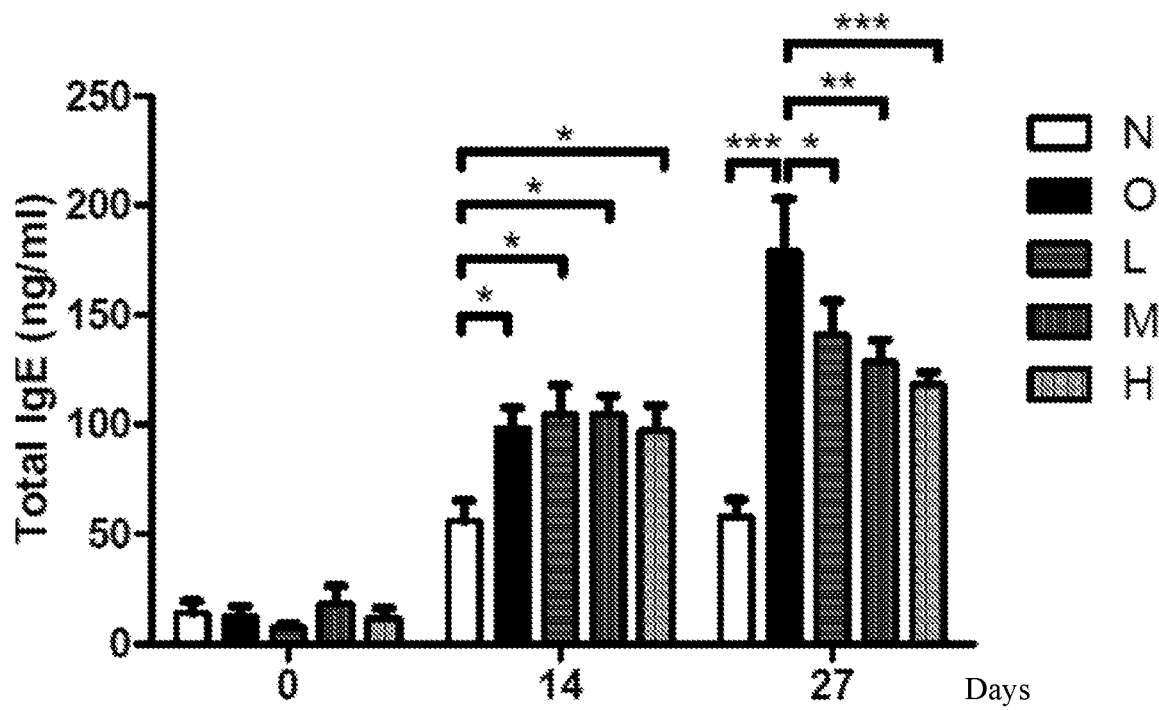
8A
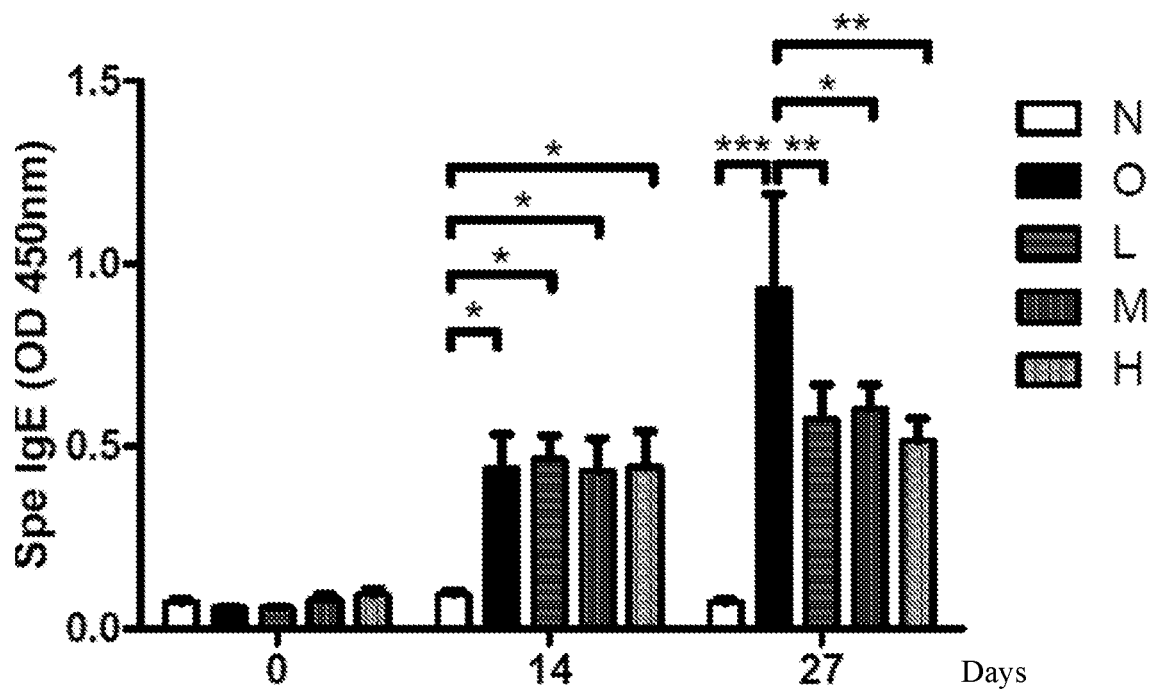
8B

FIG. 9A/B
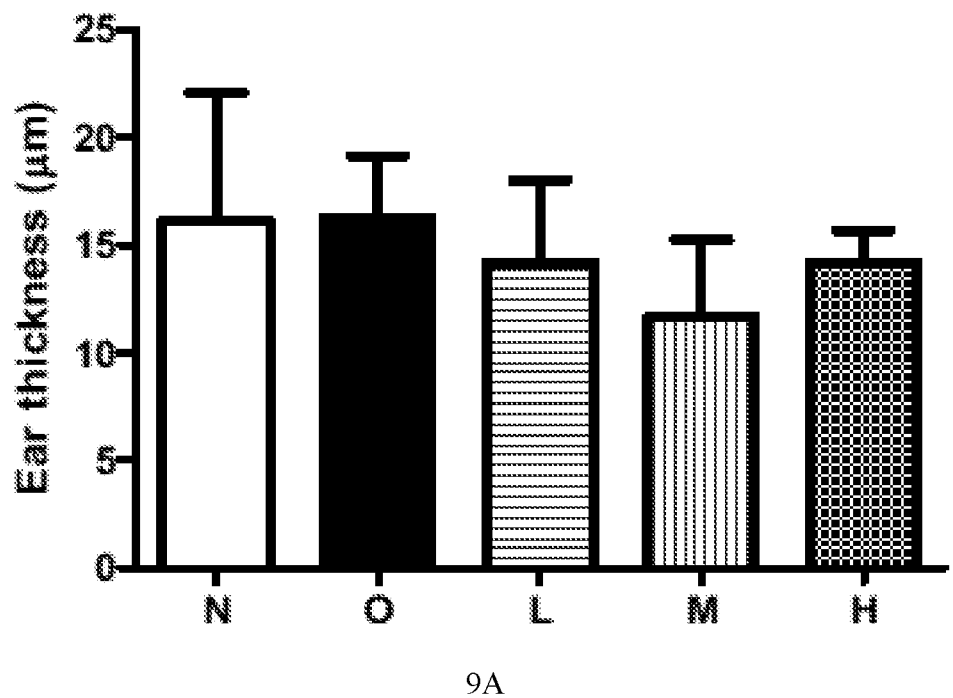
9A
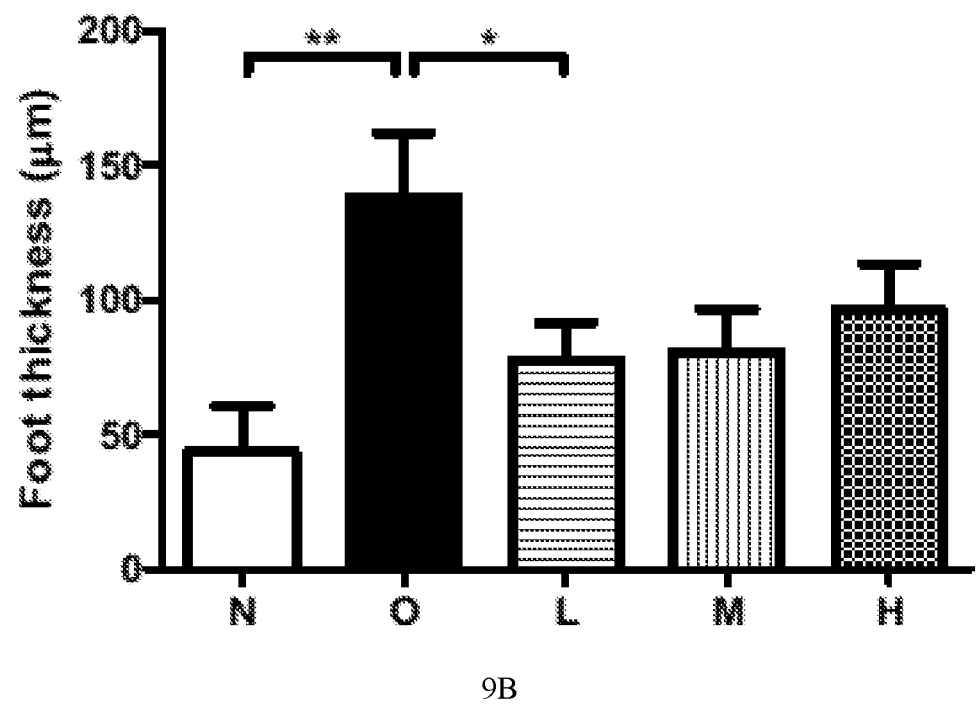
9B

FIG. 10A-D
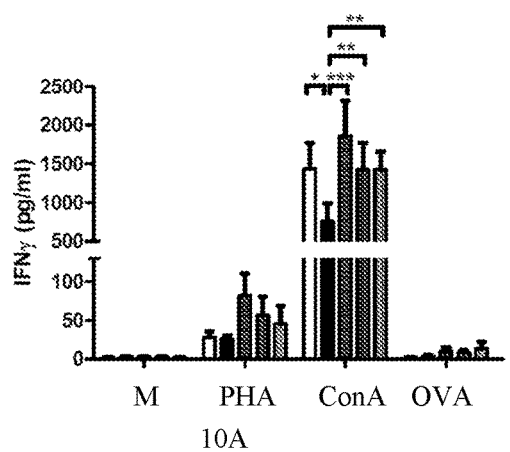
10A
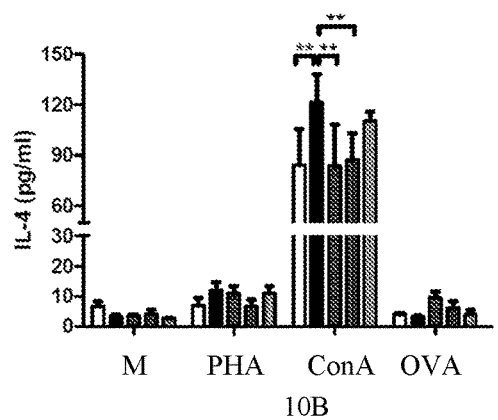
10B
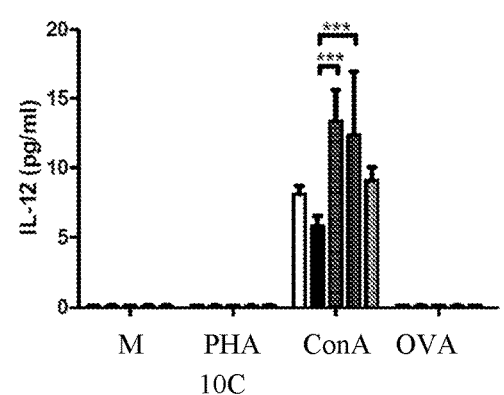
10C
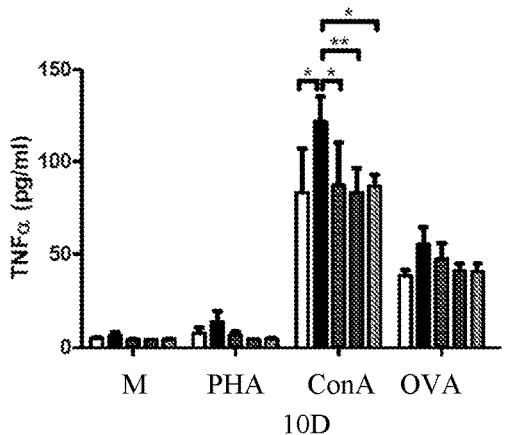
10D

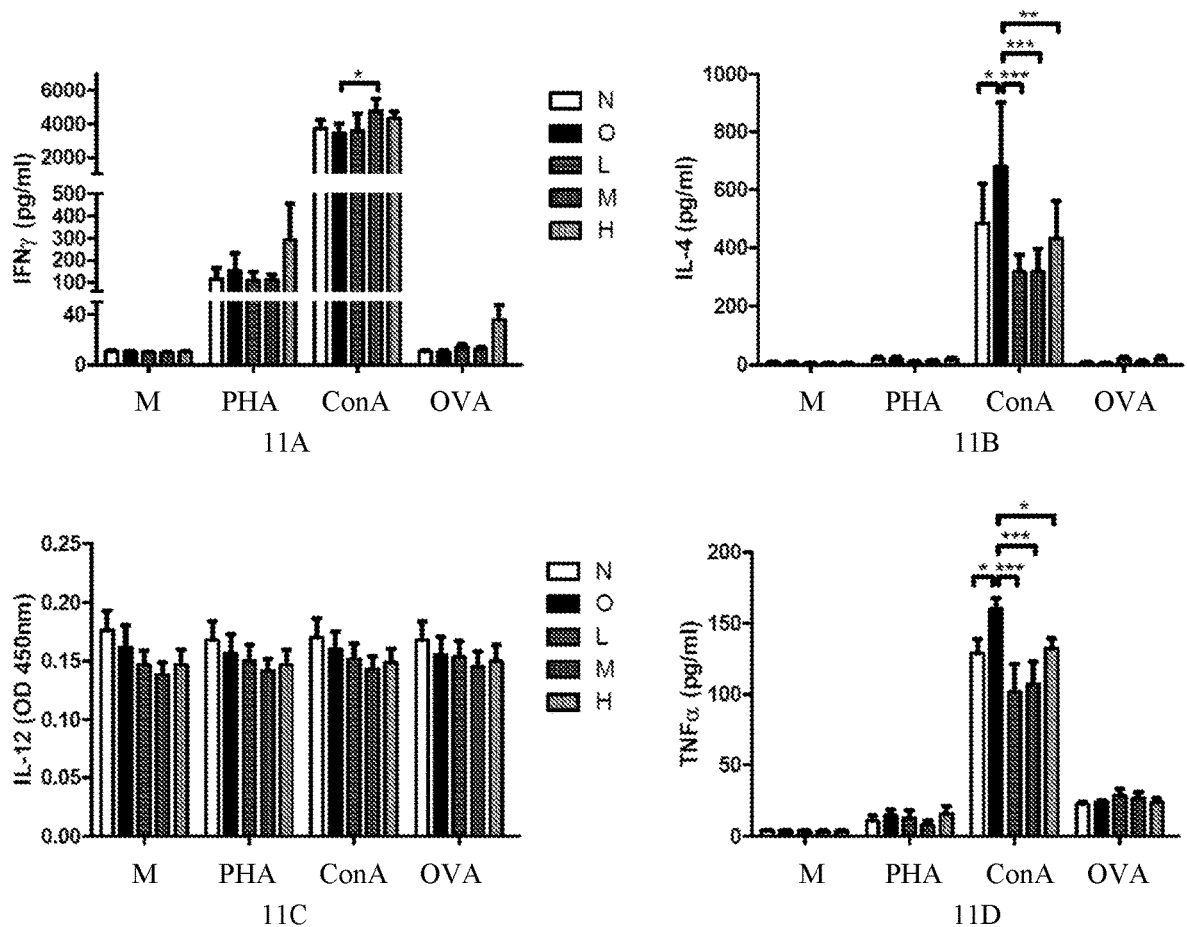
FIG. 11A-D

FIG. 12A-D
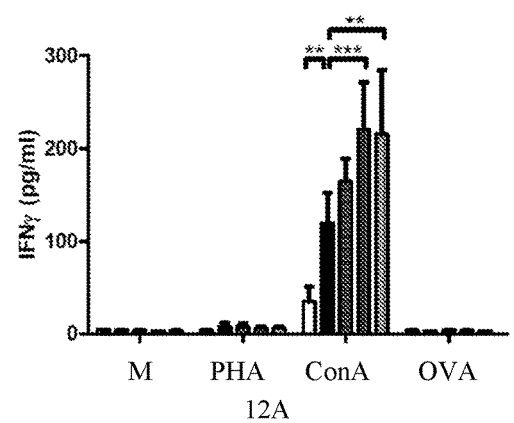
12A
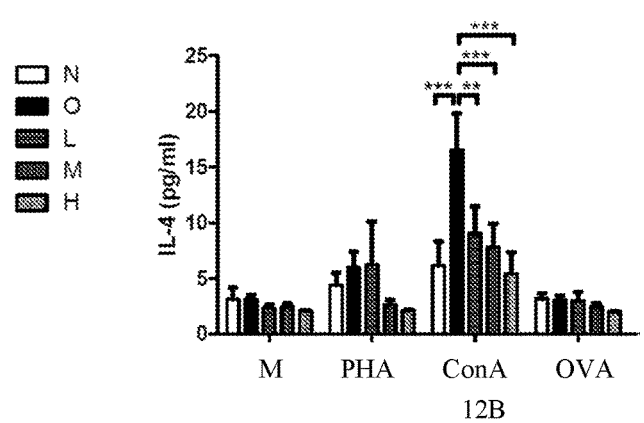
12B
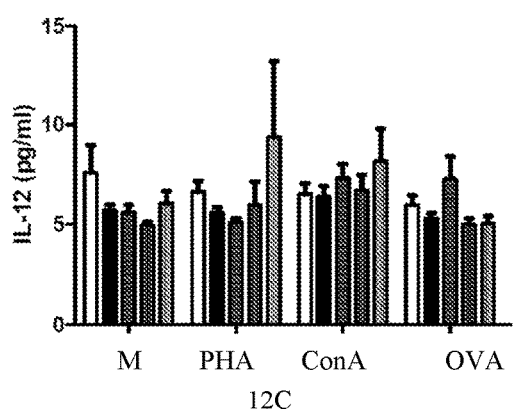
12C
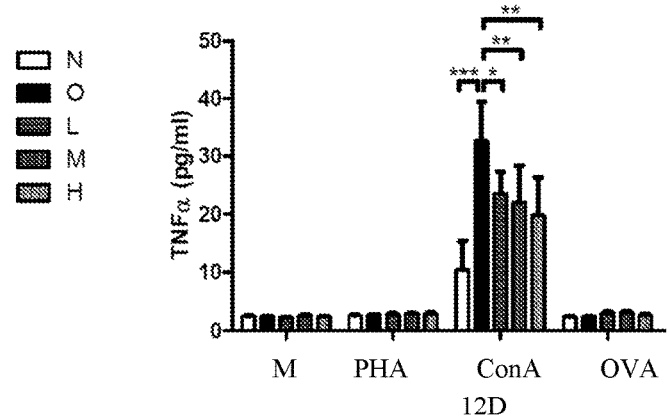
12D

FIG. 13A-D
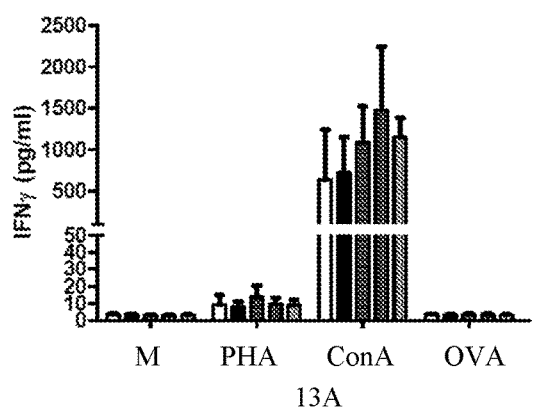
13A
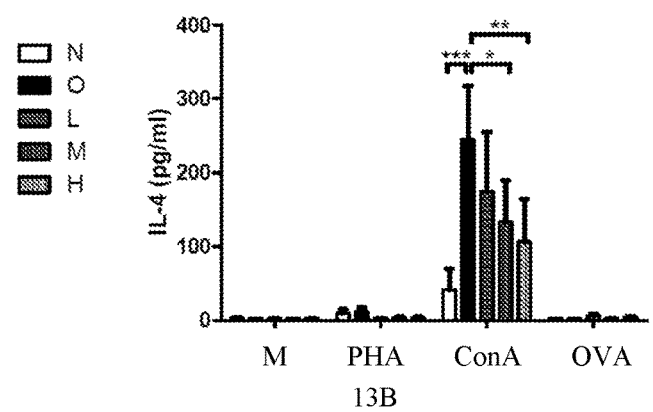
13B
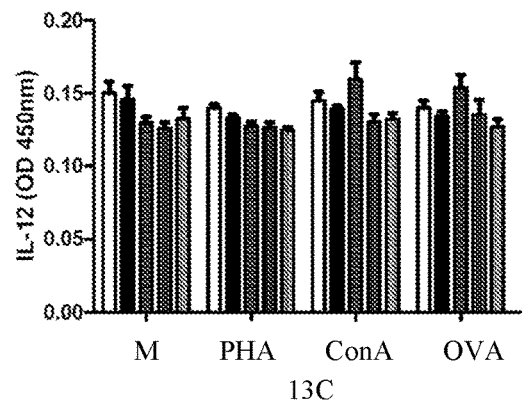
13C
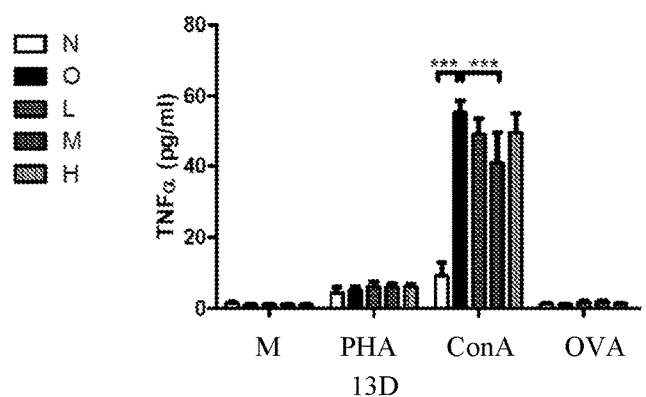
13D

METHODS AND COMPOSITIONS FOR TREATING ATOPIC DERMATITIS

BACKGROUND OF THE INVENTION

Atopic dermatitis (AD), also known as atopic eczema, is a type of inflammation of the skin (dermatitis). It results in itchy, red, swollen, and cracked skin. People with AD often have dry and scaly skin that spans the entire body, except perhaps the diaper area, and intensely itchy red, splotchy, raised lesions to form in the bends of the arms or legs, face, and neck. The condition typically starts in childhood with changing severity over the years. In children under one year of age much of the body may be affected. As people get older, the dorsal side of the knees and front of the elbows are the most common areas affected. In adults the hands and feet are the most commonly affected areas. The cause is unknown but believed to involve genetics, immune system dysfunction, environmental exposures, and difficulties with the permeability of the skin.

The diagnosis is typically based on the signs and symptoms. Other diseases that must be excluded before making a diagnosis include contact dermatitis, psoriasis, and seborrheic dermatitis. There is no known cure for AD yet, although treatments may reduce the severity and frequency of flares. Treatment involves avoiding things that make the condition worse, daily bathing with application of a moisturizing cream afterwards, applying steroid creams when flares occur, and medications to help with itchiness.

SUMMARY OF THE INVENTION

In one aspect provided herein are methods for treating or reducing the symptoms of atopic dermatitis in a subject comprising administering to said subject a therapeutically effective amount of a cyclohexenone compound having the structure:

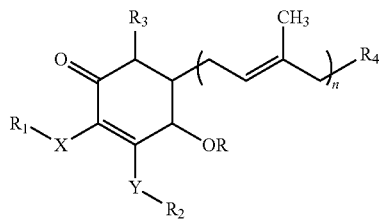

wherein each of X and Y independently is oxygen, $NR_5$ or sulfur;
R is a hydrogen or $C(=O)C_1$-$C_8$alkyl;
each of $R_1$, $R_2$ and $R_3$ independently is a hydrogen, optionally substituted methyl or $(CH_2)_m$—$CH_3$;
$R_4$ is $NR_5R_6$, $OR_5$, $OC(=O)R_7$, $C(=O)OR_5$, $C(=O)R_5$, $C(=O)NR_5R_6$, halogen, 5 or 6-membered lactone, $C_1$-$C_8$alkyl, $C_2$-$C_8$alkenyl, $C_2$-$C_8$alkynyl, aryl, glucosyl, wherein the 5 or 6-membered lactone, $C_1$-$C_8$alkyl, $C_2$-$C_8$alkenyl, $C_2$-$C_8$alkynyl, aryl, and glucosyl are optionally substituted with one or more substituents selected from $NR_5R_6$, $OR_5$, $OC(=O)R_7$, $C(=O)OR_5$, $C(=O)R_5$, $C(=O)NR_5R_6$, $C_1$-$C_8$ alkyl, $C_2$-$C_8$ alkenyl, $C_2$-$C_8$ alkynyl, $C_3$-$C_8$ cycloalkyl, and $C_1$-$C_8$ haloalkyl;
each of $R_5$ and $R_6$ is independently a hydrogen or $C_1$-$C_8$alkyl;
$R_7$ is a $C_1$-$C_8$alkyl, $OR_5$ or $NR_5R_6$;
m=1-12; and
n=1-12; or a pharmaceutically acceptable salt, metabolite, solvate or prodrug thereof.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 2A-E show illustrative skin condition changes on the back of the representative mice. 2A shows the photo of a mouse in Group N, 2B shows the photo of a mouse in the sensitized group, Group O. 2C shows the photo of a mouse in Group L (that the mice were fed with low dose of the exemplary Compound 1). 2D shows the photo of a mouse in Group M (that the mice were fed with medium dose of the exemplary Compound 1). 2E shows the photo of a mouse in Group H (that the mice were fed with high dose of the exemplary Compound 1). p value compared with N group by Student's t-test. (*p<0.05;p<0.01; * p<0.001)

FIG. 3A-C show illustrative study results of the skin conditions of relative transepidermal water loss (3A), relative humidity (3B), pH (3C) from each group. p value compared with N group by Student's t-test. (*p<0.05; p<0.01; *p<0.001)

FIG. 4A-G show the H&E stain results of the skin specimens from each group. 4A: Group N, 4B: Group O, 4C: Group L, 4D: Group M, 4E: Group H. 4F provides epidermis counts of each group. 4G provides dermis counts of each group. p value compared with N group by Student's t-test. (*p<0.05;p<0.01; * p<0.001)

FIG. 5A-F show the Eosinophil stain results of the skin specimens from each group. 5A: Group N, 5B: Group O, 5C: Group L, 5D: Group M, 5E: Group H. 5F provides eosinophil counts of each group. p value compared with N group by Student's t-test. (* p<0.05;p<0.01; *p<0.001)

FIG. 6A-F show the TSLP stain results of the skin specimens from each group. 6A: Group N, 6B: Group O, 6C: Group L, 6D: Group M, 6E: Group H. 6F provides TSLP counts of each group. p value compared with N group by Student's t-test. (*p<0.05; p<0.01; * p<0.001)

FIG. 7A-F show the Langerin stain results of the skin specimens from each group. 7A: Group N, 7B: Group O, 7C: Group L, 7D: Group M, 7E: Group H. 7F provides Langrin cell counts of each group. p value compared with N group by Student's t-test. (* p<0.05;  p<0.01; *p<0.001)

FIG. 8A/B show the results of serum immunoglobulin and OVA-specific immunoglobulin counts from each group. 8A: total IgE vs days. 8B: special IgE vs days. p value compared with N group by Student's t-test. (* p<0.05; p<0.01; * p<0.001)

FIG. 9A/B show the results of delayed sensitization reaction from each group. 9A shows the measurement of ear thickness. 9B shows the foot thickness. p value compared with N group by Student's t-test. (* $p<0.05$;  $p<0.01$; * $p<0.001$)

FIG. 10A-D show the results of spleen cell's hormone secretion simulated by PHA, ConA and OVA for 24 hours. p value compared with N group by Student's t-test. (* $p<0.05$;  $p<0.01$; * $p<0.001$)

FIG. 11A-D show the results of spleen cell's hormone secretion simulated by PHA, ConA and OVA for 72 hours. p value compared with N group by Student's t-test. (* $p<0.05$;  $p<0.01$; * $p<0.001$)

FIG. 12A-D show the results of Lymphocytes' cytokine secretion simulated by PHA, ConA and OVA for 24 hours. p value compared with N group by Student's t-test. (* $p<0.05$;  $p<0.01$; * $p<0.001$)

FIG. 13A-D show the results of Lymphocytes' cytokine secretion simulated by PHA, ConA and OVA for 72 hours. p value compared with N group by Student's t-test. (* $p<0.05$;  $p<0.01$; * $p<0.001$)

DETAILED DESCRIPTION OF THE INVENTION

Figure 1:
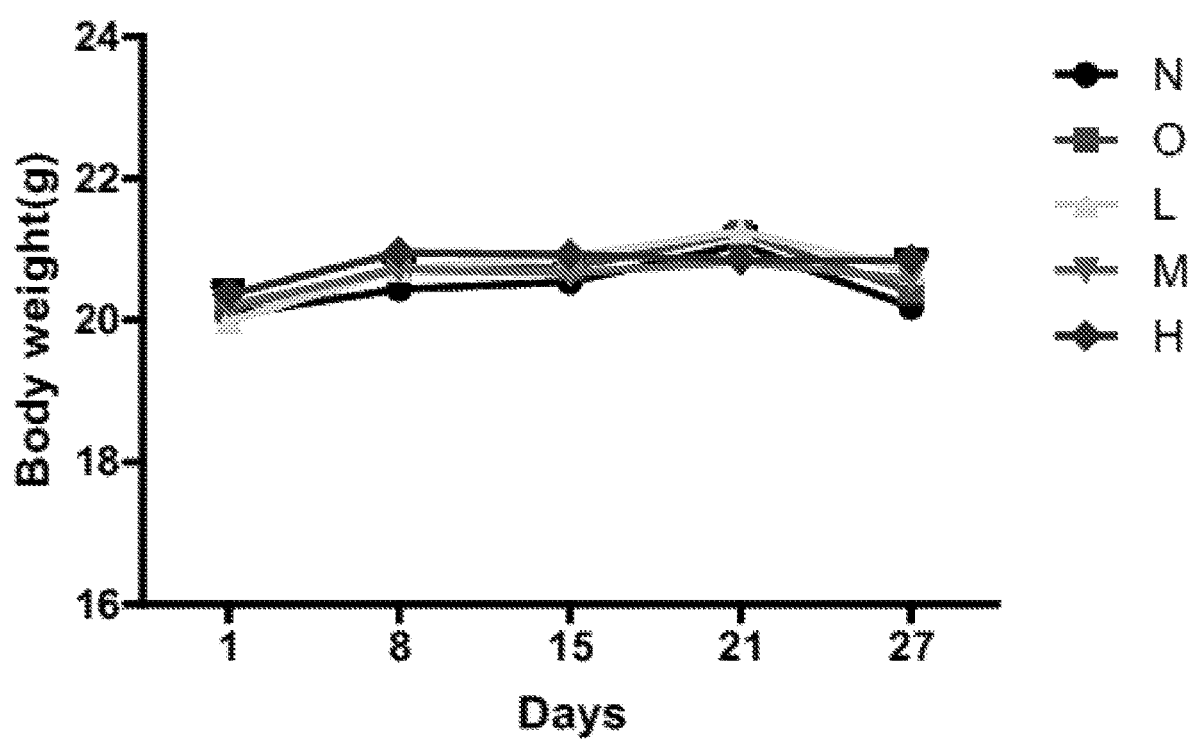
FIG. 1 shows the weight records of the mice in each group fed with various of Compound 1 during the animal study. p value compared with N group by Student's t-test. (* p<0.05; p<0.01; *p<0.001)

Atopic dermatitis (AD) is characterized by skin inflammation, damaged skin barrier function, and IgE-stimulated sensitization to environmental allergens. The immune response of atopic dermatitis (AD) can be divided as into acute and chronic phases. During the acute phase, clinical manifestation shows intense itching, erythema papules, abrasions and body fluid exudation. The pathogenesis of AD is outside-to-inside and then back to outside and has been attributed mainly to abnormalities in the regulation of T-helper 1 (Th1) TH1/TH2 cell dysregulation.

The dendritic cells in the epidermis are mainly Langerhans cells (LCs), which are myeloid dendritic cells.

The surface of the Langerhans cells has IgE and receptor FcεRI. During the acute phase, they can be exposed to environmental stimuli presented to T lymphocytes to trigger TH2 pathway, and Langerhans cells can also induce monocytes into epidermis transferring to imflammatory dendritic epidermal cells (IDEC), making IgE and receptor FcεRI to raise allergic immune responses secreting inflammatory cytokines, IL-1, IL-6, and TNF-α (Mudde G C et al., 1992; Inagaki N et al., 1997). During the chronic phase, inflammatory dendritic epidermal cells (IDEC) will transfer TH2 to TH1 and TH0 pathways causing secretion of cytokines, IFN-r, IL-12, IL-5 and GM-CSF (granulocyte macrophage colony-stimulating factor).

As reported by Leung D Y et al., Th2 cells circulating in the peripheral blood of AD patients result in elevated serum IgE and eosinophils. These T cells express the skin homing receptor, CLA, and recirculate through unaffected AD skin where they can engage allergen-triggered IgE+LCs and mast cells (MCs) that contribute to Th2 cell development. When skin injured by scratching, environmental allergens, or microbial toxins, it would activate keratinocytes to release proinflammatory cytokines and chemokines, which facilitate the extravasation of inflammatory cells into the skin. Thymic stromal lymphopoietin (TSLP) and IL-10 also enhance Th2 cell differentiation. AD inflammation causing the increase of Th2 cells in acute skin lesions. However, during chronic AD phase, it results in the infiltration of inflammatory IDECs, eosinophils and macrophages (Mφ), which produce IL-12 resulting in the switch to a Th1-type cytokine milieu associated with increased IFN-γ expression. (See "New insights into atopic dermatitis," Leung, et al., J. Clin. Invest., 2004 Mar. 1; 113(5): 651-657).

In some embodiments, provided herein are methods for treating or reducing the symptoms of atopic dermatitis in a subject by administering a cyclohexenone compound described herein to the subject (e.g. a mammal such as a rat, dog, cat, human, or the like).

The present invention found that by feeding a certain cyclohexenone compound (such as Compound 1, in low, medium, or high dose), the conditions of the mice with AD improve significantly. The improvements include for example the appearance of reduced skin inflammation, revival of skin physiological function and moisturizing effect, reduced thickness of epidermis and dermal layers of inflamed skin, and decreased Eosinophilic leukocytes and Langerhans cells infiltration phenomenon. Based on tissue staining methods, the amounts of TSLP and total IgE, which cause AD inflammation, decreased in a dose dependent manner by feeding Compound 1 to the mice with AD conditions. Based on the experiments by stimulating spleen cells and lymph node cells, the exemplary compound can also regulate certain cytokines such as increase concentrations of IFN-γ and IL-12, decrease concentrations of IL-4 and TNF-α. Thus, the cyclohexenone compounds described herein provide therapeutic benefit to a subject being treated for AD (see Examples 1-4).

The cyclohexenone compounds, in some embodiments, are obtained from extracts of natural products or prepared synthetically or semi-synthetically. In some embodiments, this invention provides the therapeutic and prophylactic potential of exemplary cyclohexenone compounds (e.g., Compound 1) for treating or reducing the symptoms of atopic dermatitis.

In some embodiments, there are provided methods for treating or reducing the symptoms of atopic dermatitis in a subject comprising administering to said subject a therapeutically effective amount of a cyclohexenone compound having the structure:

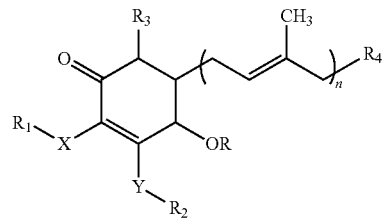

wherein each of X and Y independently is oxygen, NR$_5$ or sulfur;
R is a hydrogen or C(=O)C$_1$-C$_8$alkyl;
each of R$_1$, R$_2$ and R$_3$ independently is a hydrogen, optionally substituted methyl or (CH$_2$)$_m$—CH$_3$;
R$_4$ is NR$_5$R$_6$, OR$_5$, OC(=O)R$_7$, C(=O)R$_5$, C(=O)OR$_5$, C(=O)R$_5$, C(=O)NR$_5$R$_6$, halogen, 5 or 6-membered lactone, C$_1$-C$_8$alkyl, C$_2$-C$_8$alkenyl, C$_2$-C$_8$alkynyl, aryl, glucosyl, wherein the 5 or 6-membered lactone, C$_1$-C$_8$alkyl, C$_2$-C$_8$alkenyl, C$_2$-C$_8$alkynyl, aryl, and glucosyl are optionally substituted with one or more substituents selected from NR$_5$R$_6$, OR$_5$, OC(=O)R$_7$, C(=O)OR$_5$, C(=O)R$_5$, C(=O)NR$_5$R$_6$, C$_1$-C$_8$ alkyl, C$_2$-C$_8$ alkenyl, C$_2$-C$_8$ alkynyl, C$_3$-C$_8$ cycloalkyl, and C$_1$-C$_8$ haloalkyl;
each of R$_5$ and R$_6$ is independently a hydrogen or C$_1$-C$_8$alkyl;
R$_7$ is a C$_1$-C$_8$alkyl, OR$_5$ or NR$_5$R$_6$;
m=1-12; and
n=1-12; or a pharmaceutically acceptable salt, metabolite, solvate or prodrug thereof.

In some embodiments, there are provided pharmaceutical compositions comprising a therapeutically effective amount of a cyclohexenone compound having the structure:

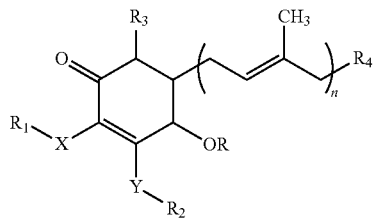

wherein each of X and Y independently is oxygen, $NR_5$ or sulfur;

R is a hydrogen or $C(=O)C_1$-$C_8$alkyl;

each of $R_1$, $R_2$ and $R_3$ independently is a hydrogen, optionally substituted methyl or $(CH_2)_m$—$CH_3$;

$R_4$ is $NR_5R_6$, $OR_5$, $OC(=O)R_7$, $C(=O)OR_5$, $C(=O)R_5$, $C(=O)NR_5R_6$, halogen, 5 or 6-membered lactone, $C_1$-$C_8$alkyl, $C_2$-$C_8$alkenyl, $C_2$-$C_8$alkynyl, aryl, glucosyl, wherein the 5 or 6-membered lactone, $C_1$-$C_8$alkyl, $C_2$-$C_8$alkenyl, $C_2$-$C_8$alkynyl, aryl, and glucosyl are optionally substituted with one or more substituents selected from $NR_5R_6$, $OR_5$, $OC(=O)R_7$, $C(=O)OR_5$, $C(=O)R_5$, $C(=O)NR_5R_6$, $C_1$-$C_8$ alkyl, $C_2$-$C_8$ alkenyl, $C_2$-$C_8$ alkynyl, $C_3$-$C_8$ cycloalkyl, and $C_1$-$C_8$ haloalkyl;

each of $R_5$ and $R_6$ is independently a hydrogen or $C_1$-$C_8$alkyl;

$R_7$ is a $C_1$-$C_8$alkyl, $OR_5$ or $NR_5R_6$;

m=1-12; and n=1-12; or a pharmaceutically acceptable salt, metabolite, solvate or prodrug thereof;

for use in treating or reducing the symptoms of atopic dermatitis in a subject.

In some embodiments, there are provided uses of a therapeutically effective amount of a cyclohexenone compound having the structure: in the manufacture of a medicament for treating or reducing the symptoms of atopic dermatitis in a subject, wherein each of X and Y independently is oxygen, $NR_5$ or sulfur;

R is a hydrogen or $C(=O)C_1$-$C_8$alkyl;

each of $R_1$, $R_2$ and $R_3$ independently is a hydrogen, optionally substituted methyl or $(CH_2)_m$—$CH_3$;

$R_4$ is $NR_5R_6$, $OR_5$, $OC(=O)R_7$, $C(=O)OR_5$, $C(=O)R_5$, $C(=O)NR_5R_6$, halogen, 5 or 6-membered lactone, $C_1$-$C_8$alkyl, $C_2$-$C_8$alkenyl, $C_2$-$C_8$alkynyl, aryl, glucosyl, wherein the 5 or 6-membered lactone, $C_1$-$C_8$alkyl, $C_2$-$C_8$alkenyl, $C_2$-$C_8$alkynyl, aryl, and glucosyl are optionally substituted with one or more substituents selected from $NR_5R_6$, $OR_5$, $OC(=O)R_7$, $C(=O)OR_5$, $C(=O)R_5$, $C(=O)NR_5R_6$, $C_1$-$C_8$ alkyl, $C_2$-$C_8$ alkenyl, $C_2$-$C_8$ alkynyl, $C_3$-$C_8$ cycloalkyl, and $C_1$-$C_8$ haloalkyl;

each of $R_5$ and $R_6$ is independently a hydrogen or $C_1$-$C_8$alkyl;

$R_7$ is a $C_1$-$C_8$alkyl, $OR_5$ or $NR_5R_6$;

m=1-12; and n=1-12; or a pharmaceutically acceptable salt, metabolite, solvate or prodrug thereof.

In some embodiments, the reducing symptoms of AD is the appearance of reduced skin inflammation, revival of skin physiological function, revival of skin moisturizing effect, reduced thickness of epidermis and dermal layers of inflamed skin, decreased Eosinophilic leukocytes and Langerhans cells infiltration phenomenon, or the like. In some embodiments, the reducing symptoms of AD is the decreased concentration of TSLP or total IgE in a subject, the increased concentration of IFN-γ or IL-12, or the decreased concentration of IL-4 or TNF-α in a subject. See Examples 2-3.

In some embodiments, the cyclohexenone compound having the structure

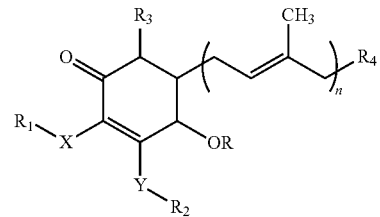

is prepared synthetically or semi-synthetically from any suitable starting material. In other embodiments, the cyclohexenone compound is prepared by fermentation, or the like. For example, Compounds 1, and 3-7 are isolated from organic solvent extracts. The non-limited exemplary compounds are illustrated below.

1

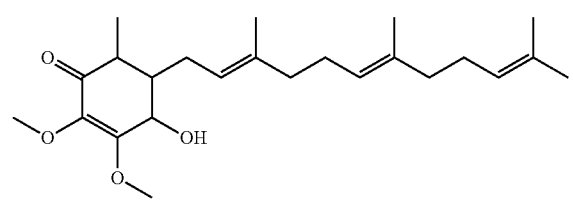

3

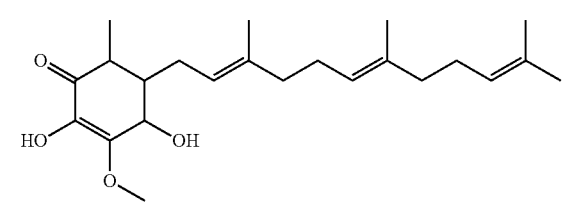

4

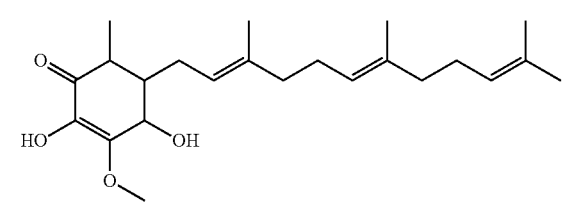

5

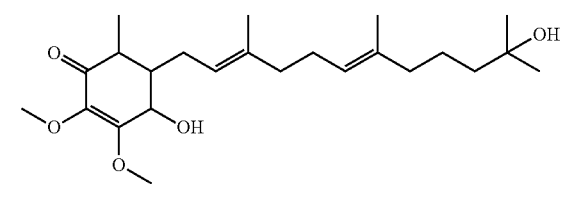

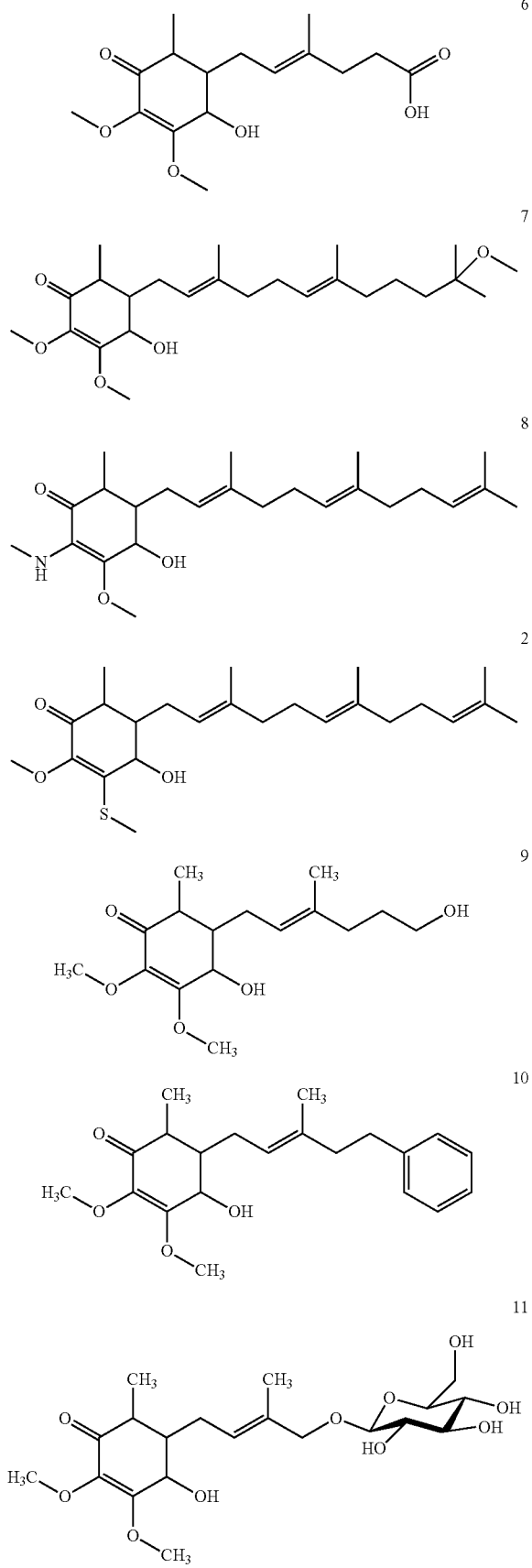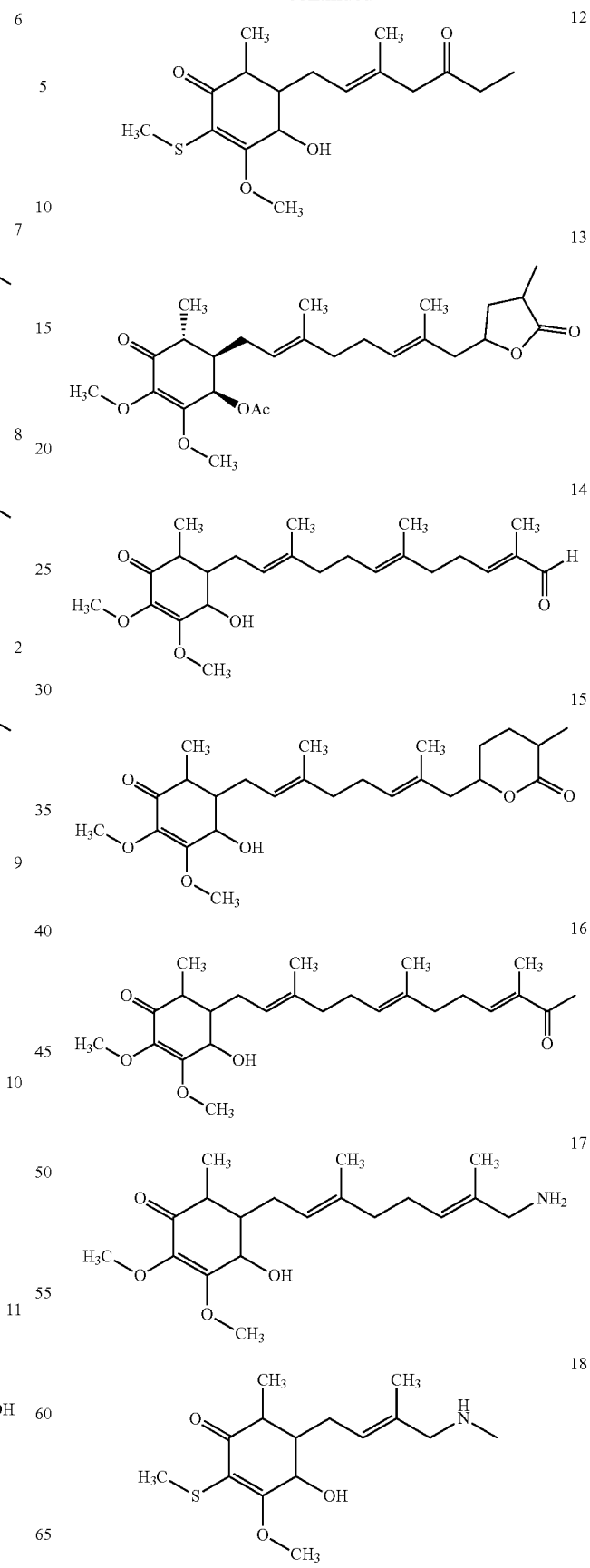

19
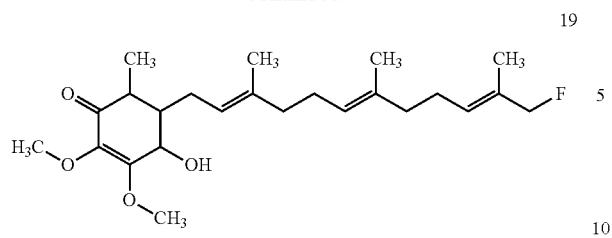
20
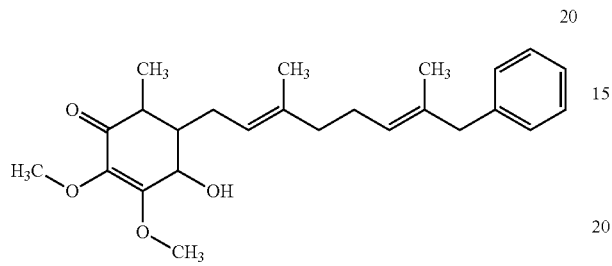
21
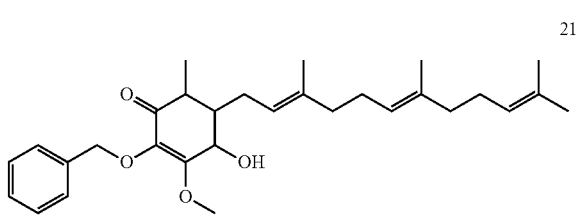
22
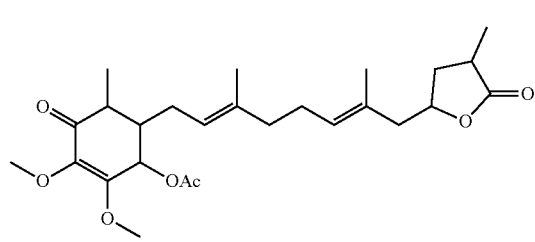
23
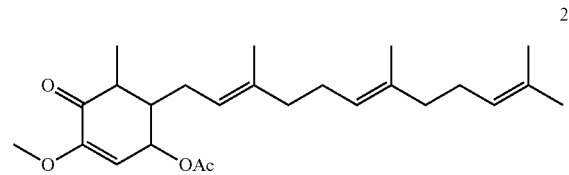
24
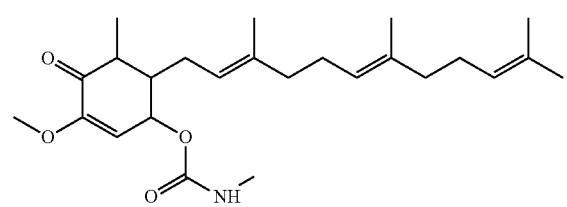
25
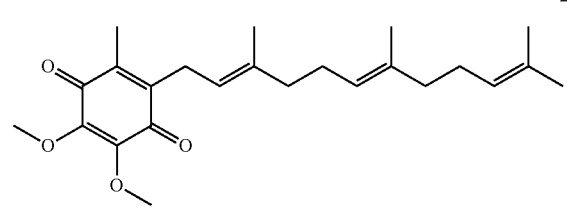
26
27
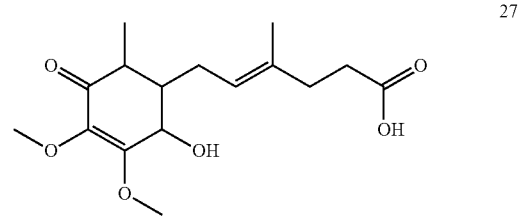
28
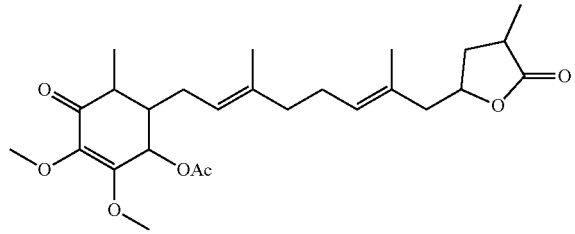
29
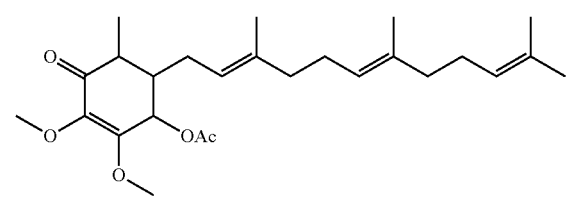
30
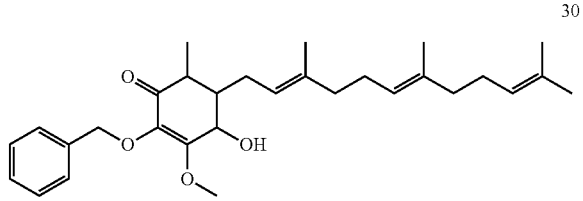
31
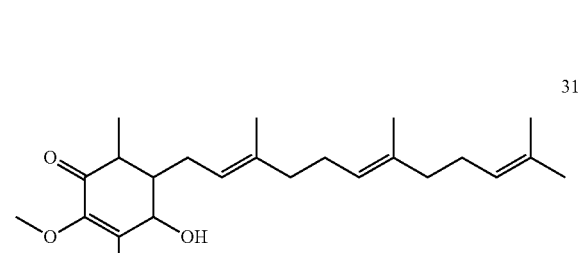
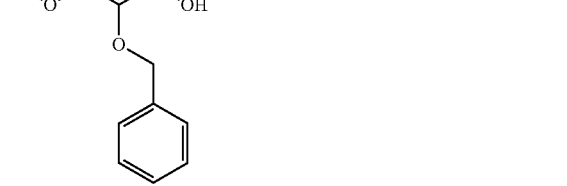

In other embodiments, the cyclohexenone compound having the structure

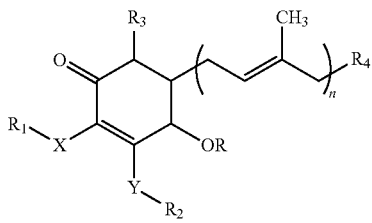

is isolated from the organic solvent extracts of *Antrodia camphorata*. In some embodiments, the organic solvent is selected from alcohols (e.g., methanol, ethanol, propanol, or the like), esters (e.g., methyl acetate, ethyl acetate, or the like), alkanes (e.g., pentane, hexane, heptane, or the like), halogenated alkanes (e.g., chloromethane, chloroethane, chloroform, methylene chloride, and the like), and the like. For example, exemplary Compounds 1-7 are isolated from organic solvent extracts. In certain embodiments, the organic solvent is alcohol. In certain embodiments, the alcohol is ethanol. In some embodiments, the cyclohexenone compound is isolated from the aqueous extracts of *Antrodia camphorata*. In certain embodiments, the cyclohexenone compounds disclosed herein are prepared synthetically or semi-synthetically.

In some embodiments, each of X and Y independently is oxygen, or sulfur. It is known in the art that a compound where each X and Y independently is sulfur can be prepared similarly or by the same route of the compound where each of X and Y independently is oxygen, because oxygen and sulfur share similar chemical property in a structure. In some embodiments, by a proper protecting group, the compound where each of X and Y independently is $NR_5$ can be prepared by the similar route of a compound where each of X and Y independently is oxygen or sulfur.

In some embodiments, R is a hydrogen, $C(=O)C_3H_8$, $C(=O)C_2H_5$, or $C(=O)CH_3$. In some embodiments, $R_1$ is a hydrogen, methyl, ethyl, propyl, butyl, pentyl or hexyl. In certain embodiments, $R_1$ is a hydrogen or methyl. In some embodiments, $R_2$ is a hydrogen, methyl, ethyl, propyl, butyl, pentyl or hexyl. In certain embodiments, $R_2$ is a hydrogen or methyl. In some embodiments, $R_3$ is a hydrogen, methyl, ethyl, propyl, butyl, pentyl or hexyl. In some embodiments, $R_4$ is halogen, $NH_2$, $NHCH_3$, $N(CH_3)_2$, $OCH_3$, $OC_2H_5$, $C(=O)CH_3$, $C(=O)C_2H_5$, $C(=O)OCH_3$, $C(=O)OC_2H_5$, $C(=O)NHCH_3$, $C(=O)NHC_2H_5$, $C(=O)NH_2$, $OC(=O)$ $CH_3$, $OC(=O)C_2H_5$, $OC(=O)OCH_3$, $OC(=O)OC_2H_5$, $OC(=O)NHCH_3$, $OC(=O)NHC_2H_5$, or $OC(=O)NH_2$. In some embodiments, $R_4$ is $C_2H_5C(CH_3)_2OH$, $C_2H_5C(CH_3)_2$ $OCH_3$, $CH_2COOH$, $C_2H_5COOH$, $CH_2OH$, $C_2H_5OH$, $CH_2Ph$, $C_2H_5Ph$, $CH_2CH=C(CH_3)(CHO)$, $CH_2CH=C$ $(CH_3)(C(=O)CH_3)$, 5 or 6-membered lactone, $C_2$-$C_8$alkenyl, $C_2$-$C_8$alkynyl, aryl, and glucosyl, wherein 5 or 6-membered lactone, $C_2$-$C_8$alkenyl, $C_2$-$C_8$alkynyl, aryl, and glucosyl are optionally substituted with one or more substituents selected from $NR_5R_6$, $OR_5$, $OC(=O)R_7$, $C(=O)OR_5$, $C(=O)R_5$, $C(=O)NR_5R_6$, $C_1$-$C_8$ alkyl, $C_2$-$C_8$ alkenyl, $C_2$-$C_8$ alkynyl, $C_3$-$C_8$ cycloalkyl, and $C_1$-$C_8$ haloalkyl. In certain embodiments, $R_4$ is 5 or 6-membered lactone, $C_2$-$C_8$alkenyl, $C_2$-$C_8$alkynyl, aryl, and glucosyl, optionally substituted with one or more substituents selected from $NR_5R_6$, $OR_5$, $OC(=O)R_7$, $C(=O)OR_5$, $C(=O)R_5$, $C(=O)$ $NR_5R_6$, $C_1$-$C_8$ alkyl, $C_2$-$C_8$ alkenyl, $C_2$-$C_8$ alkynyl, $C_3$-$C_8$ cycloalkyl, and $C_1$-$C_8$ haloalkyl. In certain embodiments, $R_4$ is $CH_2CH=C(CH_3)_2$. In certain embodiments, the compound is

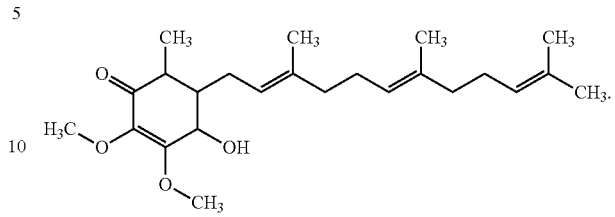

Certain Pharmaceutical and Medical Terminology

Unless otherwise stated, the following terms used in this application, including the specification and claims, have the definitions given below. It must be noted that, as used in the specification and the appended claims, the singular forms "a," "an" and "the" include plural referents unless the context clearly dictates otherwise. Unless otherwise indicated, conventional methods of mass spectroscopy, NMR, HPLC, protein chemistry, biochemistry, recombinant DNA techniques and pharmacology are employed. In this application, the use of "or" or "and" means "and/or" unless stated otherwise. Furthermore, use of the term "including" as well as other forms, such as "include", "includes," and "included," is not limiting. The section headings used herein are for organizational purposes only and are not to be construed as limiting the subject matter described.

An "alkyl" group refers to an aliphatic hydrocarbon group. The alkyl group may be a saturated alkyl group (which means that it does not contain any carbon-carbon double bonds or carbon-carbon triple bonds) or the alkyl group may be an unsaturated alkyl group (which means that it contains at least one carbon-carbon double bonds or carbon-carbon triple bond). The alkyl moiety, whether saturated or unsaturated, may be branched, or straight chain.

The "alkyl" group may have 1 to 12 carbon atoms (whenever it appears herein, a numerical range such as "1 to 12 refers to each integer in the given range; e.g., "1 to 12 carbon atoms" means that the alkyl group may consist of 1 carbon atom, 2 carbon atoms, 3 carbon atoms, etc., up to and including 12 carbon atoms, although the present definition also covers the occurrence of the term "alkyl" where no numerical range is designated). The alkyl group of the compounds described herein may be designated as "$C_1$-$C_8$ alkyl" or similar designations. By way of example only, "$C_1$-$C_8$ alkyl" indicates that there are one, two, three, four, five, six, seven or eight carbon atoms in the alkyl chain. In one aspect the alkyl is selected from the group consisting of methyl, ethyl, propyl, iso-propyl, n-butyl, iso-butyl, sec-butyl, and t-butyl. Typical alkyl groups include, but are in no way limited to, methyl, ethyl, propyl, isopropyl, butyl, isobutyl, sec-butyl, tertiary butyl, pentyl, neopentyl, hexyl, allyl, but-2-enyl, but-3-enyl, cyclopropylmethyl, cyclobutylmethyl, cyclopentylmethyl, cyclohexylmethyl, and the like. In one aspect, an alkyl is a $C_1$-$C_8$ alkyl.

The term "alkylene" refers to a divalent alkyl radical. Any of the above mentioned monovalent alkyl groups may be an alkylene by abstraction of a second hydrogen atom from the alkyl. In one aspect, an alkylene is a $C_1$-$C_{12}$alkylene. In another aspect, an alkylene is a $C_1$-$C_8$alkylene. Typical alkylene groups include, but are not limited to, —$CH_2$—, —$CH(CH_3)$—, —$C(CH_3)_2$—, —$CH_2CH_2$—, —$CH_2CH$ $(CH_3)$—, —$CH_2C(CH_3)_2$—, —$CH_2CH_2CH_2$—, —$CH_2$ $CH_2CH_2CH_2$—, and the like.

As used herein, the term "aryl" refers to an aromatic ring wherein each of the atoms forming the ring is a carbon atom. Aryl rings are formed by five, six, seven, eight, nine, or more than nine carbon atoms. Aryl groups are optionally substituted. In one aspect, an aryl is a phenyl or a naphthalenyl. In one aspect, an aryl is a phenyl. In one aspect, an aryl is a $C_6$-$C_{10}$aryl. Depending on the structure, an aryl group can be a monoradical or a diradical (i.e., an arylene group). In one aspect, an arylene is a $C_6$-$C_{10}$ arylene. Exemplary arylenes include, but are not limited to, phenyl-1,2-ene, phenyl-1,3-ene, and phenyl-1,4-ene.

The term "aromatic" refers to a planar ring having a delocalized π-electron system containing 4n+2 π electrons, where n is an integer. Aromatic rings can be formed from five, six, seven, eight, nine, ten, or more than ten atoms. Aromatics are optionally substituted. The term "aromatic" includes both carbocyclic aryl ("aryl", e.g., phenyl) and heterocyclic aryl (or "heteroaryl" or "heteroaromatic") groups (e.g., pyridine). The term includes monocyclic or fused-ring polycyclic (i.e., rings which share adjacent pairs of carbon atoms) groups.

The term "halo" or, alternatively, "halogen" or "halide" means fluoro, chloro, bromo or iodo.

The term "lactone" refers to a cyclic ester which can be seen as the condensation product of an alcohol group —OH and a carboxylic acid group —COOH in the same molecule. It is characterized by a closed ring consisting of two or more carbon atoms and a single oxygen atom, with a ketone group =O in one of the carbons adjacent to the other oxygen.

The term "heterocycle" or "heterocyclic" refers to heteroaromatic rings (also known as heteroaryls) and heterocycloalkyl rings (also known as heteroalicyclic groups) containing one to four heteroatoms in the ring(s), where each heteroatom in the ring(s) is selected from O, S and N, wherein each heterocyclic group has from 4 to 10 atoms in its ring system, and with the proviso that the any ring does not contain two adjacent O or S atoms. Non-aromatic heterocyclic groups (also known as heterocycloalkyls) include groups having only 3 atoms in their ring system, but aromatic heterocyclic groups must have at least 5 atoms in their ring system. The heterocyclic groups include benzo-fused ring systems. An example of a 3-membered heterocyclic group is aziridinyl. An example of a 4-membered heterocyclic group is azetidinyl. An example of a 5-membered heterocyclic group is thiazolyl. An example of a 6-membered heterocyclic group is pyridyl, and an example of a 10-membered heterocyclic group is quinolinyl. Examples of non-aromatic heterocyclic groups are pyrrolidinyl, tetrahydrofuranyl, dihydrofuranyl, tetrahydrothienyl, oxazolidinonyl, tetrahydropyranyl, dihydropyranyl, tetrahydrothiopyranyl, piperidinyl, morpholinyl, thiomorpholinyl, thioxanyl, piperazinyl, aziridinyl, azetidinyl, oxetanyl, thietanyl, homopiperidinyl, oxepanyl, thiepanyl, oxazepinyl, diazepinyl, thiazepinyl, 1,2,3,6-tetrahydropyridinyl, pyrrolin-2-yl, pyrrolin-3-yl, indolinyl, 2H-pyranyl, 4H-pyranyl, dioxanyl, 1,3-dioxolanyl, pyrazolinyl, dithianyl, dithiolanyl, dihydropyranyl, dihydrothienyl, dihydrofuranyl, pyrazolidinyl, imidazolinyl, imidazolidinyl, 3-azabicyclo[3.1.0]hexanyl, 3-azabicyclo[4.1.0]heptanyl, 3H-indolyl and quinolizinyl. Examples of aromatic heterocyclic groups are pyridinyl, imidazolyl, pyrimidinyl, pyrazolyl, triazolyl, pyrazinyl, tetrazolyl, furyl, thienyl, isoxazolyl, thiazolyl, oxazolyl, isothiazolyl, pyrrolyl, quinolinyl, isoquinolinyl, indolyl, benzimidazolyl, benzofuranyl, cinnolinyl, indazolyl, indolizinyl, phthalazinyl, pyridazinyl, triazinyl, isoindolyl, pteridinyl, purinyl, oxadiazolyl, thiadiazolyl, furazanyl, benzofurazanyl, benzothiophenyl, benzothiazolyl, benzoxazolyl, quinazolinyl, quinoxalinyl, naphthyridinyl, and furopyridinyl. The foregoing groups may be C-attached or N-attached where such is possible. For instance, a group derived from pyrrole may be pyrrol-1-yl (N-attached) or pyrrol-3-yl (C-attached). Further, a group derived from imidazole may be imidazol-1-yl or imidazol-3-yl (both N-attached) or imidazol-2-yl, imidazol-4-yl or imidazol-5-yl (all C-attached). The heterocyclic groups include benzo-fused ring systems. Non-aromatic heterocycles may be substituted with one or two oxo (=O) moieties, such as pyrrolidin-2-one.

The term "alkenyl" as used herein, means a straight, branched chain, or cyclic (in which case, it would also be known as a "cycloalkenyl") hydrocarbon containing from 2-10 carbons and containing at least one carbon-carbon double bond formed by the removal of two hydrogens. In some embodiments, depending on the structure, an alkenyl group is a monoradical or a diradical (i.e., an alkenylene group). In some embodiments, alkenyl groups are optionally substituted. Illustrative examples of alkenyl include, but are not limited to, ethenyl, 2-propenyl, 2-methyl-2-propenyl, 3-butenyl, 4-pentenyl, 5-hexenyl, 2-heptenyl, 2-methyl-1-heptenyl, and 3-cecenyl.

The term "alkynyl" as used herein, means a straight, branched chain, or cyclic (in which case, it would also be known as a "cycloalkynyl") hydrocarbon containing from 2-10 carbons and containing at least one carbon-carbon triple bond formed by the removal of four hydrogens. In some embodiments, depending on the structure, an alkynyl group is a monoradical or a diradical (i.e., an alkynylene group). In some embodiments, alkynyl groups are optionally substituted. Illustrative examples of alkynyl include, but are not limited to, ethynyl, propynyl, butynyl, pentynyl, hexynyl, heptynyl, and the like.

The term "alkoxy" as used herein, means an alkyl group, as defined herein, appended to the parent molecular moiety through an oxygen atom. Illustrative examples of alkoxy include, but are not limited to, methoxy, ethoxy, propoxy, 2-propoxy, butoxy, tert-butoxy, pentyloxy, and hexyloxy.

The term "cycloalkyl" as used herein, means a monocyclic or polycyclic radical that contains only carbon and hydrogen, and includes those that are saturated, partially unsaturated, or fully unsaturated. Cycloalkyl groups include groups having from 3 to 10 ring atoms. Representative examples of cyclic include but are not limited to, the following moieties:

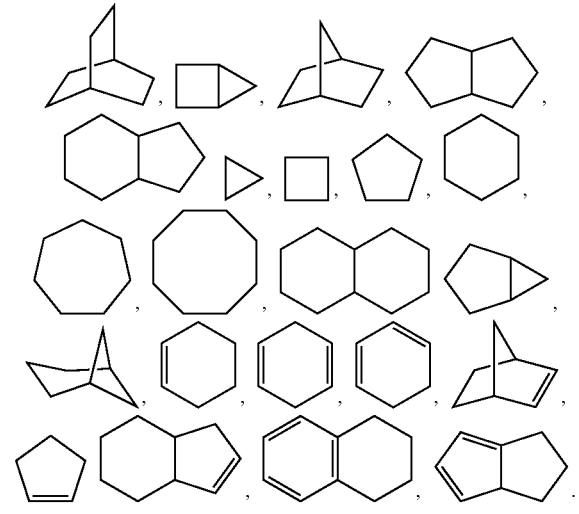

In some embodiments, depending on the structure, a cycloalkyl group is a monoradical or a diradical (e.g., a cycloalkylene group).

The terms "haloalkyl," "haloalkenyl," "haloalkynyl" and "haloalkoxy" as used herein, include alkyl, alkenyl, alkynyl and alkoxy structures in which at least one hydrogen is replaced with a halogen atom. In certain embodiments in which two or more hydrogen atoms are replaced with halogen atoms, the halogen atoms are all the same as one another. In other embodiments in which two or more hydrogen atoms are replaced with halogen atoms, the halogen atoms are not all the same as one another. The terms "fluoroalkyl" and "fluoroalkoxy" include haloalkyl and haloalkoxy groups, respectively, in which the halo is fluorine. In certain embodiments, haloalkyls are optionally substituted.

The term "glucosyl" as used herein, include D- or L-form glucosyl groups, in which the glucosyl group is attached via any hydroxyl group on the glucose ring.

The term "acceptable" with respect to a formulation, composition or ingredient, as used herein, means having no persistent detrimental effect on the general health of the subject being treated.

*Antrodia* is a genus of fungi in the family Meripilaceae. *Antrodia* species have fruiting bodies that typically lie flat or spread out on the growing surface, with the hymenium exposed to the outside; the edges may be turned so as to form narrow brackets. Most species are found in temperate and boreal forests, and cause brown rot.

*Antrodia camphorata*, also known as stout camphor fungus, *Ganoderma camphoratum*, is a species of *Antrodia* fungi, that is endemic to Taiwan, where it grows only on the endemic tree *Cinnamomum kanehirae*, causing a brown heart rot. This unique mushroom of Taiwan has been used as a traditional medicine for protection of different disease conditions.

It is known in the art that the active ingredients isolated from the different parts of *Antrodia camphorata* vary by different cultural medium, and methods. For example, certain cyclohexenone compounds disclosed herein can be isolated from the unique solid state fermentation process to cultivate *Antrodia camphorata* which is different from other known methods.

The term "carrier," as used herein, refers to relatively nontoxic chemical compounds or agents that facilitate the incorporation of a compound into cells or tissues.

The terms "co-administration" or the like, as used herein, are meant to encompass administration of the selected therapeutic agents to a single patient, and are intended to include treatment regimens in which the agents are administered by the same or different route of administration or at the same or different time.

The term "diluent" refers to chemical compounds that are used to dilute the compound of interest prior to delivery. Diluents can also be used to stabilize compounds because they can provide a more stable environment. Salts dissolved in buffered solutions (which also can provide pH control or maintenance) are utilized as diluents in the art, including, but not limited to a phosphate buffered saline solution.

The terms "effective amount" or "therapeutically effective amount," as used herein, refer to a sufficient amount of an agent or a compound being administered which will relieve to some extent one or more of the symptoms of the disease or condition being treated. The result can be reduction and/or alleviation of the signs, symptoms, or causes of a disease, or any other desired alteration of a biological system. For example, an "effective amount" for therapeutic uses is the amount of the composition comprising a compound as disclosed herein required to provide a clinically significant decrease in disease symptoms. An appropriate "effective" amount in any individual case may be determined using techniques, such as a dose escalation study.

The terms "enhance" or "enhancing," as used herein, means to increase or prolong either in potency or duration a desired effect. Thus, in regard to enhancing the effect of therapeutic agents, the term "enhancing" refers to the ability to increase or prolong, either in potency or duration, the effect of other therapeutic agents on a system. An "enhancing-effective amount," as used herein, refers to an amount adequate to enhance the effect of another therapeutic agent in a desired system.

A "metabolite" of a compound disclosed herein is a derivative of that compound that is formed when the compound is metabolized. The term "active metabolite" refers to a biologically active derivative of a compound that is formed when the compound is metabolized. The term "metabolized," as used herein, refers to the sum of the processes (including, but not limited to, hydrolysis reactions and reactions catalyzed by enzymes) by which a particular substance is changed by an organism. Thus, enzymes may produce specific structural alterations to a compound. For example, cytochrome P450 catalyzes a variety of oxidative and reductive reactions while uridine diphosphate glucuronyltransferases catalyze the transfer of an activated glucuronic-acid molecule to aromatic alcohols, aliphatic alcohols, carboxylic acids, amines and free sulphydryl groups. Metabolites of the compounds disclosed herein are optionally identified either by administration of compounds to a host and analysis of tissue samples from the host, or by incubation of compounds with hepatic cells in vitro and analysis of the resulting compounds.

The term "pharmaceutical combination" as used herein, means a product that results from the mixing or combining of more than one active ingredient and includes both fixed and non-fixed combinations of the active ingredients. The term "fixed combination" means that the active ingredients, e.g. a compound (i.e., a cyclohexenone compound described herein) and a co-agent, are both administered to a patient simultaneously in the form of a single entity or dosage. The term "non-fixed combination" means that the active ingredients, e.g. a compound (i.e., a cyclohexenone compound described herein) and a co-agent, are administered to a patient as separate entities either simultaneously, concurrently or sequentially with no specific intervening time limits, wherein such administration provides effective levels of the two compounds in the body of the patient. The latter also applies to cocktail therapy, e.g. the administration of three or more active ingredients.

The term "pharmaceutical composition" refers to a mixture of a compound (i.e., a cyclohexenone compound described herein) with other chemical components, such as carriers, stabilizers, diluents, dispersing agents, suspending agents, thickening agents, and/or excipients. The pharmaceutical composition facilitates administration of the compound to an organism. Multiple techniques of administering a compound exist in the art including, but not limited to: intravenous, oral, aerosol, parenteral, ophthalmic, pulmonary and topical administration.

The term "subject" or "patient" encompasses mammals. Examples of mammals include, but are not limited to, any member of the Mammalian class: humans, non-human primates such as chimpanzees, and other apes and monkey species; farm animals such as cattle, horses, sheep, goats, swine; domestic animals such as rabbits, dogs, and cats;

laboratory animals including rodents, such as rats, mice and guinea pigs, and the like. In one embodiment, the mammal is a human.

The terms "treat," "treating" or "treatment," as used herein, include alleviating, abating or ameliorating at least one symptom of a disease or condition, preventing additional symptoms, inhibiting the disease or condition, e.g., arresting the development of the disease or condition, relieving the disease or condition, causing regression of the disease or condition, relieving a condition caused by the disease or condition, or stopping the symptoms of the disease or condition either prophylactically and/or therapeutically.

Routes of Administration and Dosage

Suitable routes of administration include, but are not limited to, oral, intravenous, rectal, aerosol, parenteral, ophthalmic, pulmonary, transmucosal, transdermal, vaginal, otic, nasal, and topical administration. In addition, by way of example only, parenteral delivery includes intramuscular, subcutaneous, intravenous, intramedullary injections, as well as intrathecal, direct intraventricular, intraperitoneal, intralymphatic, and intranasal injections.

In certain embodiments, a compound as described herein is administered in a local rather than systemic manner, for example, via injection of the compound directly into an organ, often in a depot preparation or sustained release formulation. In specific embodiments, long acting formulations are administered by implantation (for example subcutaneously or intramuscularly) or by intramuscular injection. Furthermore, in other embodiments, the drug is delivered in a targeted drug delivery system, for example, in a liposome coated with organ-specific antibody. In such embodiments, the liposomes are targeted to and taken up selectively by the organ. In yet other embodiments, the compound as described herein is provided in the form of a rapid release formulation, in the form of an extended release formulation, or in the form of an intermediate release formulation. In yet other embodiments, the compound described herein is administered topically.

In some embodiments, the cyclohexenone compound, or a pharmaceutically acceptable salt, metabolite, solvate or prodrug thereof, is administered parenterally or intravenously. In other embodiments, the cyclohexenone compound, or a pharmaceutically acceptable salt, metabolite, solvate or prodrug thereof, is administered by injection. In some embodiments, the cyclohexenone compound, or a pharmaceutically acceptable salt, metabolite, solvate or prodrug thereof, is administered orally.

In the case wherein the patient's condition does not improve, upon the doctor's discretion the administration of the compounds may be administered chronically, that is, for an extended period of time, including throughout the duration of the patient's life in order to ameliorate or otherwise control or limit the symptoms of the patient's disease or condition. In the case wherein the patient's status does improve, upon the doctor's discretion the administration of the compounds may be given continuously or temporarily suspended for a certain length of time (i.e., a "drug holiday").

The foregoing ranges are merely suggestive, as the number of variables in regard to an individual treatment regime is large, and considerable excursions from these recommended values are not uncommon. Such dosages may be altered depending on a number of variables, not limited to the activity of the compound used, the disease or condition to be treated, the mode of administration, the requirements of the individual subject, the severity of the disease or condition being treated, and the judgment of the practitioner.

Toxicity and therapeutic efficacy of such therapeutic regimens can be determined by standard pharmaceutical procedures in cell cultures or experimental animals, including, but not limited to, for determining the $LD_{50}$ (the dose lethal to 50% of the population) and the $ED_{50}$ (the dose therapeutically effective in 50% of the population). The dose ratio between the toxic and therapeutic effects is the therapeutic index and it can be expressed as the ratio between $LD_{50}$ and $ED_{50}$. Compounds exhibiting high therapeutic indices are preferred. The data obtained from cell culture assays and animal studies can be used in formulating a range of dosage for use in human. The dosage of such compounds lies preferably within a range of circulating concentrations that include the $ED_{50}$ with minimal toxicity. The dosage may vary within this range depending upon the dosage form employed and the route of administration utilized.

Pharmaceutical Formulation

In some embodiments provide pharmaceutical compositions comprising a therapeutically effective amount of a cyclohexenone compound having the structure:

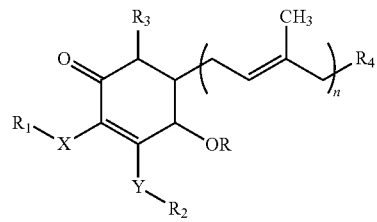

wherein each of X and Y independently is oxygen, $NR_5$ or sulfur;

R is a hydrogen or $C(=O)C_1$-$C_8$alkyl;

each of $R_1$, $R_2$ and $R_3$ independently is a hydrogen, optionally substituted methyl or $(CH_2)_m$—$CH_3$;

$R_4$ is $NR_5R_6$, $OR_5$, $OC(=O)R_7$, $C(=O)OR_5$, $C(=O)R_5$, $C(=O)NR_5R_6$, halogen, 5 or 6-membered lactone, $C_1$-$C_8$alkyl, $C_2$-$C_8$alkenyl, $C_2$-$C_8$alkynyl, aryl, glucosyl, wherein the 5 or 6-membered lactone, $C_1$-$C_8$alkyl, $C_2$-$C_8$alkenyl, $C_2$-$C_8$alkynyl, aryl, and glucosyl are optionally substituted with one or more substituents selected from $NR_5R_6$, $OR_5$, $OC(=O)R_7$, $C(=O)OR_5$, $C(=O)R_5$, $C(=O)NR_5R_6$, $C_1$-$C_8$ alkyl, $C_2$-$C_8$ alkenyl, $C_2$-$C_8$ alkynyl, $C_3$-$C_8$ cycloalkyl, and $C_1$-$C_8$ haloalkyl;

each of $R_5$ and $R_6$ is independently a hydrogen or $C_1$-$C_8$alkyl;

$R_7$ is a $C_1$-$C_8$alkyl, $OR_5$ or $NR_5R_6$;

m=1-12; and n=1-12; or a pharmaceutically acceptable salt, metabolite, solvate or prodrug thereof; and a pharmaceutically acceptable excipient.

In some embodiments, the cyclohexenone compounds of the pharmaceutical compositions have the structure:

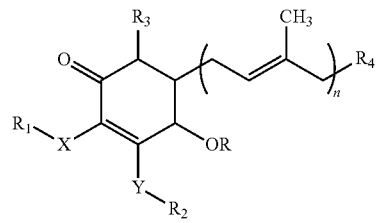

wherein each of X and Y independently is oxygen, $NR_5$ or sulfur;

R is a hydrogen or $C(=O)C_1$-$C_8$alkyl;

each of $R_1$, $R_2$ and $R_3$ independently is a hydrogen, optionally substituted methyl or $(CH_2)_m$—$CH_3$;

$R_4$ is $NR_5R_6$, $OR_5$, $OC(=O)R_7$, $C(=O)OR_5$, $C(=O)R_5$, $C(=O)NR_5R_6$, halogen, 5 or 6-membered lactone, $C_1$-$C_8$alkyl, $C_2$-$C_8$alkenyl, $C_2$-$C_8$alkynyl, aryl, glucosyl, wherein the 5 or 6-membered lactone, $C_1$-$C_8$alkyl, $C_2$-$C_8$alkenyl, $C_2$-$C_8$alkynyl, aryl, and glucosyl are optionally substituted with one or more substituents selected from $NR_5R_6$, $OR_5$, $OC(=O)R_7$, $C(=O)OR_5$, $C(=O)R_5$, $C(=O)NR_5R_6$, $C_1$-$C_8$ alkyl, $C_2$-$C_8$ alkenyl, $C_2$-$C_8$ alkynyl, $C_3$-$C_8$ cycloalkyl, and $C_1$-$C_8$ haloalkyl;

each of $R_5$ and $R_6$ is independently a hydrogen or $C_1$-$C_8$alkyl;

$R_7$ is a $C_1$-$C_8$alkyl, $OR_5$ or $NR_5R_6$;

m=1-12; and n=1-12; or a pharmaceutically acceptable salt, metabolite, solvate or prodrug thereof.

In some embodiments, R is a hydrogen, $C(=O)C_3H_8$, $C(=O)C_2H_5$, or $C(=O)CH_3$. In some embodiments, each of $R_1$, $R_2$ and $R_3$ independently is a hydrogen, methyl, ethyl, propyl, butyl, pentyl hexyl, heptyl, or octyl. In certain embodiments, $R_1$ is a hydrogen or methyl. In certain embodiments, $R_2$ is a hydrogen, methyl, ethyl, propyl, butyl, pentyl or hexyl. In certain embodiments, $R_3$ is a hydrogen, methyl, ethyl, propyl, butyl, pentyl or hexyl. In some embodiments, $R_4$ is halogen, $NH_2$, $NHCH_3$, $N(CH_3)_2$, $OCH_3$, $OC_2H_5$, $C(=O)CH_3$, $C(=O)C_2H_5$, $C(=O)OCH_3$, $C(=O)OC_2H_5$, $C(=O)NHCH_3$, $C(=O)NHC_2H_5$, $C(=O)NH_2$, $OC(=O)CH_3$, $OC(=O)C_2H_5$, $OC(=O)OCH_3$, $OC(=O)OC_2H_5$, $OC(=O)NHCH_3$, $OC(=O)NHC_2H_5$, or $OC(=O)NH_2$. In certain embodiments, $R_4$ is $C_2H_5C(CH_3)_2$ OH, $C_2H_5C(CH_3)_2OCH_3$, $CH_2COOH$, $C_2H_5COOH$, $CH_2OH$, $C_2H_5OH$, $CH_2Ph$, $C_2H_5Ph$, $CH_2CH=C(CH_3)$ (CHO), $CH_2CH=C(CH_3)(C(=O)CH_3)$, 5 or 6-membered lactone, aryl, or glucosyl, wherein the 5 or 6-membered lactone, aryl, and glucosyl are optionally substituted with one or more substituents selected from $NR_5R_6$, $OR_5$, $OC(=O)R_7$, $C(=O)OR_5$, $C(=O)R_5$, $C(=O)NR_5R_6$, $C_1$-$C_8$ alkyl, $C_2$-$C_8$ alkenyl, $C_2$-$C_8$ alkynyl, $C_3$-$C_8$ cycloalkyl, and $C_1$-$C_8$ haloalkyl. In certain embodiments, $R_4$ is $CH_2COOH$, $C_2H_5COOH$, $CH_2OH$, $C_2H_5OH$, $CH_2Ph$, $C_2H_5Ph$, $CH_2CH=C(CH_3)(CH_0)$, $CH_2CH=C(CH_3)(C(=O)CH_3)$, 5 or 6-membered lactone, aryl, or glucosyl, wherein 5 or 6-membered lactone, aryl, and glucosyl are optionally substituted with one or more substituents selected from $NR_5R_6$, $OR_5$, $OC(=O)R_7$, $C(=O)OR_5$, $C(=O)R_5$, $C(=O)NR_5R_6$, $C_1$-$C_8$ alkyl, $C_2$-$C_8$ alkenyl, $C_2$-$C_8$ alkynyl, $C_3$-$C_8$ cycloalkyl, and $C_r$-$C_8$ haloalkyl. In certain embodiments, $R_4$ is 5 or 6-membered lactone, aryl, or glucosyl, optionally substituted with one or more substituents selected from $NR_5R_6$, $OR_5$, $OC(=O)R_7$, $C(=O)OR_5$, $C(=O)R_5$, $C(=O)NR_5R_6$, $C_1$-$C_8$ alkyl, $C_2$-$C_8$ alkenyl, $C_2$-$C_8$ alkynyl, $C_3$-$C_8$ cycloalkyl, and $C_1$-$C_8$ haloalkyl.

In certain embodiments, the compound is selected from group consisting of

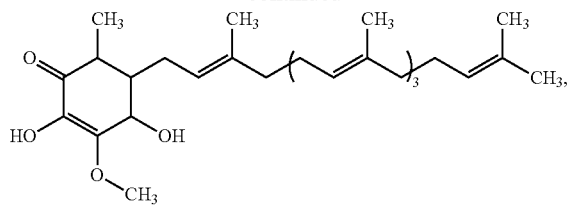

-continued

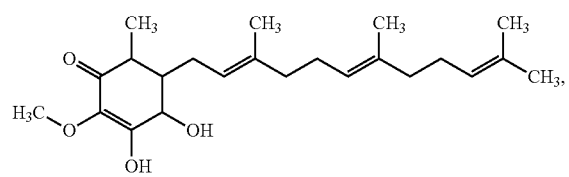

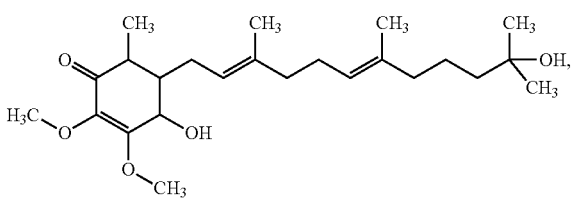

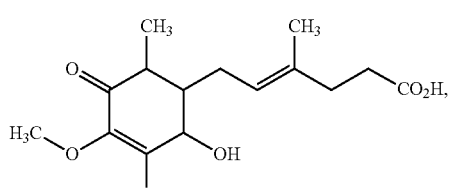

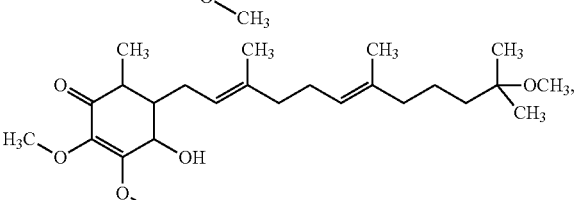

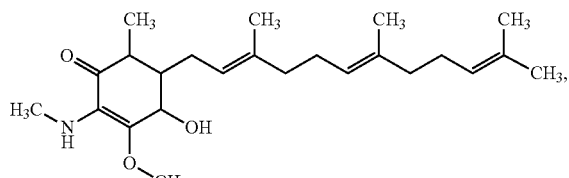

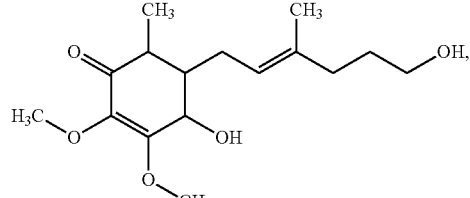

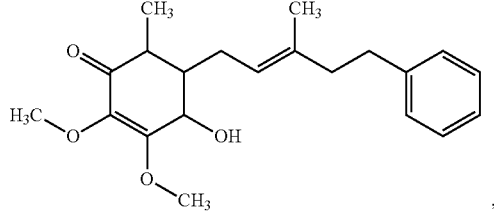

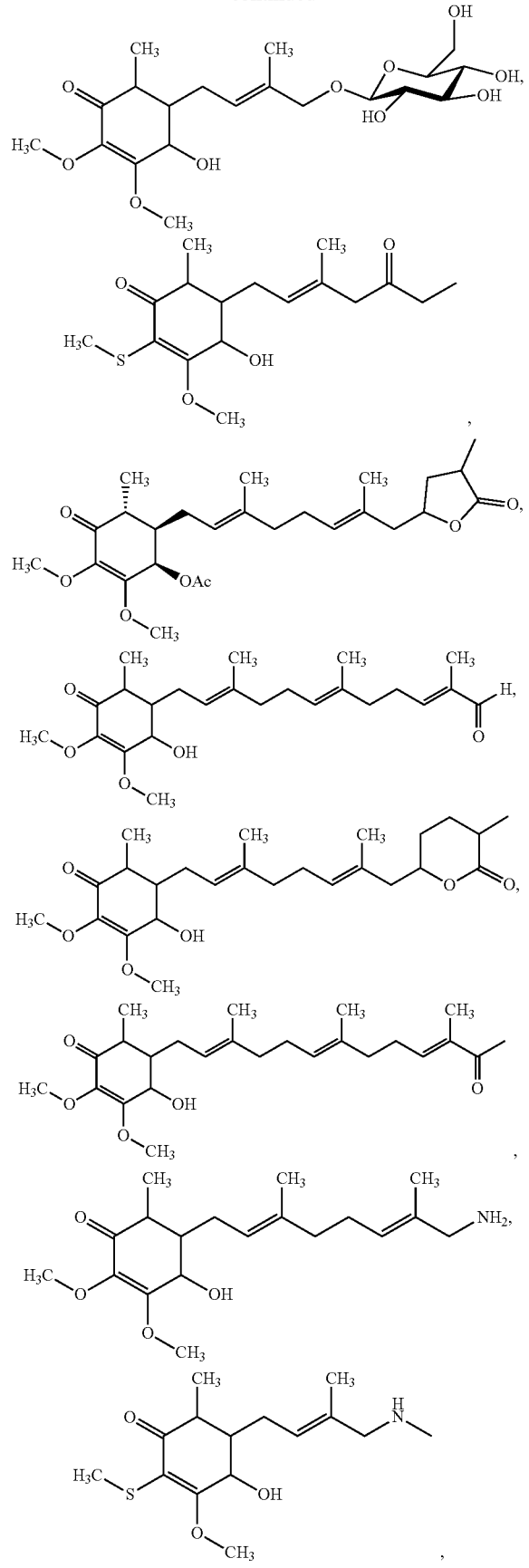
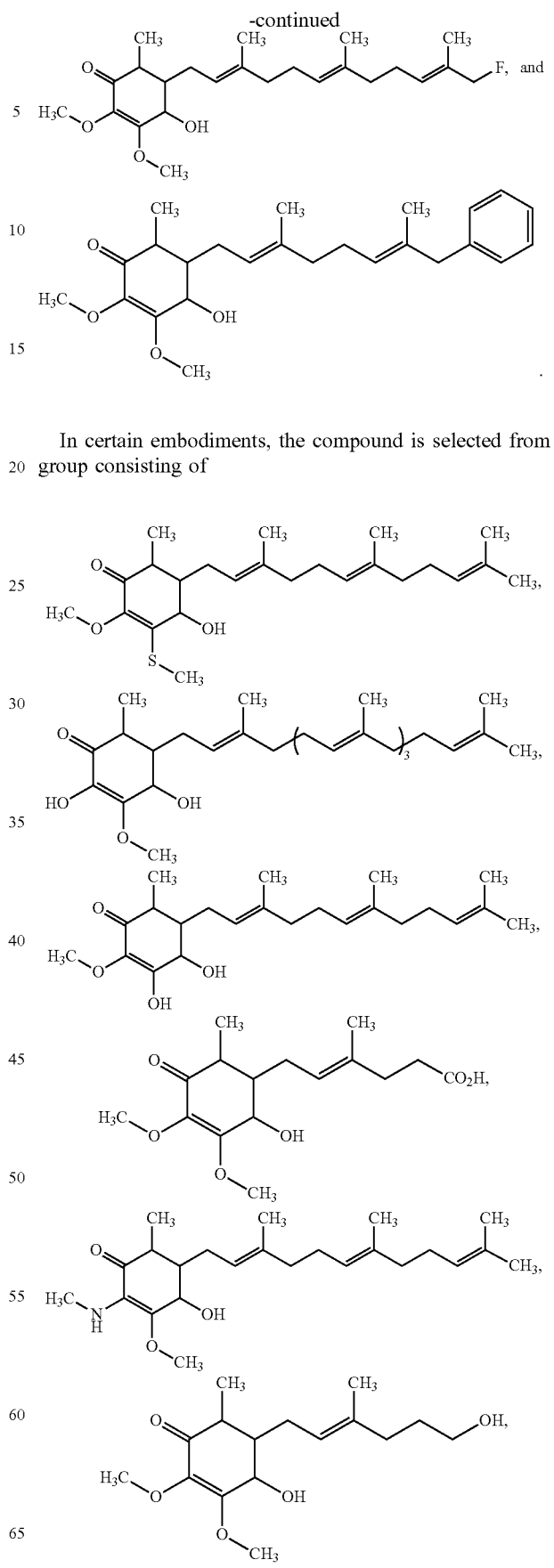
In certain embodiments, the compound is selected from group consisting of

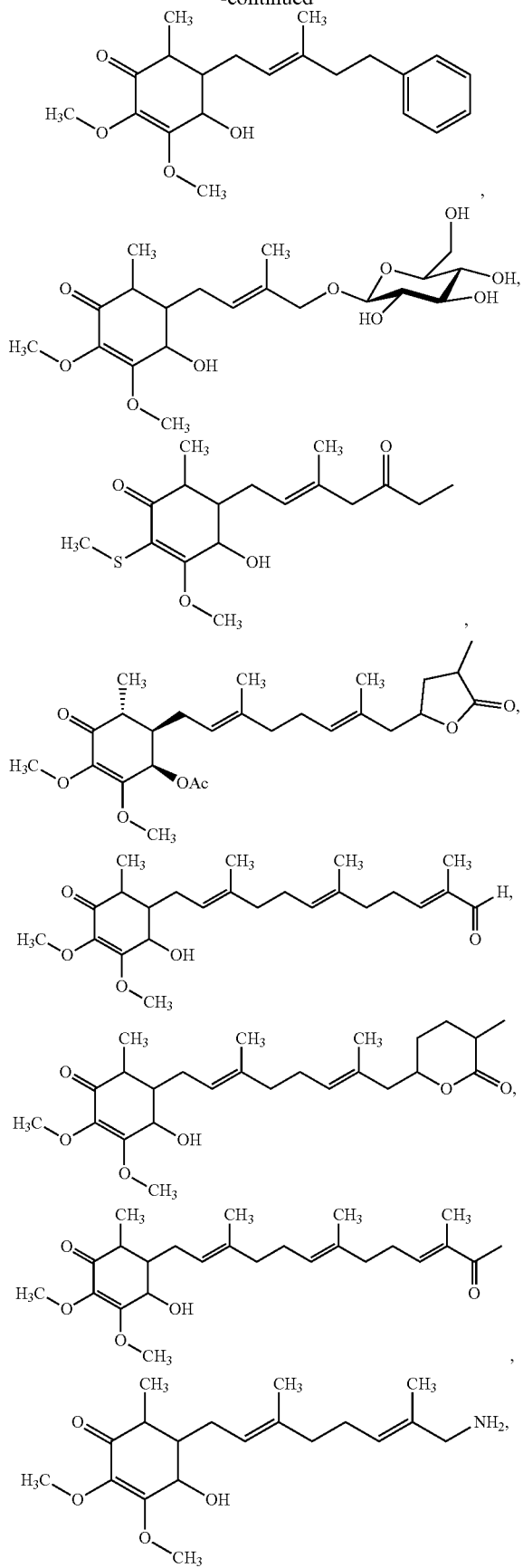

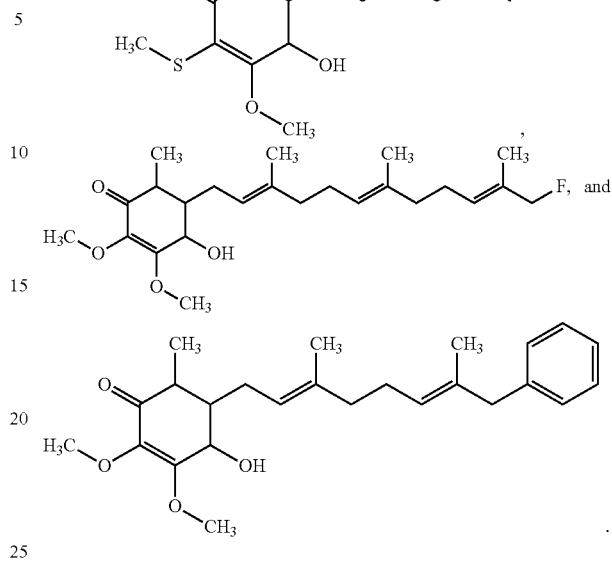

In some embodiments, the compounds described herein are formulated into pharmaceutical compositions. In specific embodiments, pharmaceutical compositions are formulated in a conventional manner using one or more physiologically acceptable carriers comprising excipients and auxiliaries which facilitate processing of the active compounds into preparations which can be used pharmaceutically. Proper formulation is dependent upon the route of administration chosen. Any pharmaceutically acceptable techniques, carriers, and excipients are used as suitable to formulate the pharmaceutical compositions described herein: *Remington: The Science and Practice of Pharmacy*, Nineteenth Ed (Easton, Pa.: Mack Publishing Company, 1995); Hoover, John E., *Remington's Pharmaceutical Sciences*, Mack Publishing Co., Easton, Pa. 1975; Liberman, H. A. and Lachman, L., Eds., *Pharmaceutical Dosage Forms*, Marcel Decker, New York, N.Y., 1980; and *Pharmaceutical Dosage Forms and* Drug Delivery Systems, Seventh Ed. (Lippincott Williams & Wilkins 1999).

Provided herein are pharmaceutical compositions comprising a compound (i.e., a cyclohexenone compound described herein) and a pharmaceutically acceptable diluent(s), excipient(s), or carrier(s). In certain embodiments, the compounds described are administered as pharmaceutical compositions in which a compound (i.e., a cyclohexenone compound described herein) is mixed with other active ingredients, as in combination therapy. Encompassed herein are all combinations of actives set forth in the combination therapies section below and throughout this disclosure. In specific embodiments, the pharmaceutical compositions include one or more compounds (i.e., a cyclohexenone compound described herein).

A pharmaceutical composition, as used herein, refers to a mixture of a compound (i.e., a cyclohexenone compound described herein) with other chemical components, such as carriers, stabilizers, diluents, dispersing agents, suspending agents, thickening agents, and/or excipients. In certain embodiments, the pharmaceutical composition facilitates administration of the compound to an organism. In some embodiments, practicing the methods of treatment or use provided herein, therapeutically effective amounts of compounds (i.e., a cyclohexenone compound described herein) are administered in a pharmaceutical composition to a mammal having a disease or condition to be treated. In specific embodiments, the mammal is a human. In certain embodiments, therapeutically effective amounts vary depending on the severity of the disease, the age and relative health of the subject, the potency of the compound used and other factors. The compounds described herein are used singly or in combination with one or more therapeutic agents as components of mixtures.

In one embodiment, a compound (i.e., a cyclohexenone compound described herein) is formulated in an aqueous solution. In specific embodiments, the aqueous solution is selected from, by way of example only, a physiologically compatible buffer, such as Hank's solution, Ringer's solution, or physiological saline buffer. In other embodiments, a compound (i.e., a cyclohexenone compound described herein) is formulated for transmucosal administration. In specific embodiments, transmucosal formulations include penetrants that are appropriate to the barrier to be permeated. In still other embodiments wherein the compounds described herein are formulated for other parenteral injections, appropriate formulations include aqueous or nonaqueous solutions. In specific embodiments, such solutions include physiologically compatible buffers and/or excipients.

In another embodiment, compounds described herein are formulated for oral administration. Compounds described herein, including a compound (i.e., a cyclohexenone compound described herein), are formulated by combining the active compounds with, e.g., pharmaceutically acceptable carriers or excipients. In various embodiments, the compounds described herein are formulated in oral dosage forms that include, by way of example only, tablets, powders, pills, dragees, capsules, liquids, gels, syrups, elixirs, slurries, suspensions and the like.

In certain embodiments, pharmaceutical preparations for oral use are obtained by mixing one or more solid excipients with one or more of the compounds described herein, optionally grinding the resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as: for example, maize starch, wheat starch, rice starch, potato starch, gelatin, gum tragacanth, methylcellulose, microcrystalline cellulose, hydroxypropylmethylcellulose, sodium carboxymethylcellulose; or others such as: polyvinylpyrrolidone (PVP or povidone) or calcium phosphate. In specific embodiments, disintegrating agents are optionally added. Disintegrating agents include, by way of example only, cross-linked croscarmellose sodium, polyvinylpyrrolidone, agar, or alginic acid or a salt thereof such as sodium alginate.

In one embodiment, dosage forms, such as dragee cores and tablets, are provided with one or more suitable coating. In specific embodiments, concentrated sugar solutions are used for coating the dosage form. The sugar solutions, optionally contain additional components, such as by way of example only, gum arabic, talc, polyvinylpyrrolidone, carbopol gel, polyethylene glycol, and/or titanium dioxide, lacquer solutions, and suitable organic solvents or solvent mixtures. Dyestuffs and/or pigments are also optionally added to the coatings for identification purposes. Additionally, the dyestuffs and/or pigments are optionally utilized to characterize different combinations of active compound doses.

In certain embodiments, therapeutically effective amounts of at least one of the compounds described herein are formulated into other oral dosage forms. Oral dosage forms include push-fit capsules made of gelatin, as well as soft, sealed capsules made of gelatin and a plasticizer, such as glycerol or sorbitol. In specific embodiments, push-fit capsules contain the active ingredients in admixture with one or more filler. Fillers include, by way of example only, lactose, binders such as starches, and/or lubricants such as talc or magnesium stearate and, optionally, stabilizers. In other embodiments, soft capsules, contain one or more active compound that is dissolved or suspended in a suitable liquid. Suitable liquids include, by way of example only, one or more fatty oil, liquid paraffin, or liquid polyethylene glycol. In addition, stabilizers are optionally added.

In other embodiments, therapeutically effective amounts of at least one of the compounds described herein are formulated for buccal or sublingual administration. Formulations suitable for buccal or sublingual administration include, by way of example only, tablets, lozenges, or gels. In still other embodiments, the compounds described herein are formulated for parental injection, including formulations suitable for bolus injection or continuous infusion. In specific embodiments, formulations for injection are presented in unit dosage form (e.g., in ampoules) or in multi-dose containers. Preservatives are, optionally, added to the injection formulations. In still other embodiments, the pharmaceutical compositions of a compound (i.e., a cyclohexenone compound described herein) are formulated in a form suitable for parenteral injection as a sterile suspensions, solutions or emulsions in oily or aqueous vehicles. Parenteral injection formulations optionally contain formulatory agents such as suspending, stabilizing and/or dispersing agents. In specific embodiments, pharmaceutical formulations for parenteral administration include aqueous solutions of the active compounds in water-soluble form. In additional embodiments, suspensions of the active compounds are prepared as appropriate oily injection suspensions. Suitable lipophilic solvents or vehicles for use in the pharmaceutical compositions described herein include, by way of example only, fatty oils such as sesame oil, or synthetic fatty acid esters, such as ethyl oleate or triglycerides, or liposomes. In certain specific embodiments, aqueous injection suspensions contain substances which increase the viscosity of the suspension, such as sodium carboxymethyl cellulose, sorbitol, or dextran. Optionally, the suspension contains suitable stabilizers or agents which increase the solubility of the compounds to allow for the preparation of highly concentrated solutions. Alternatively, in other embodiments, the active ingredient is in powder form for constitution with a suitable vehicle, e.g., sterile pyrogen-free water, before use.

In one aspect, compounds (i.e., cyclohexenone compounds described herein) are prepared as solutions for parenteral injection as described herein or known in the art and administered with an automatic injector. Automatic injectors, such as those disclosed in U.S. Pat. Nos. 4,031,893, 5,358,489; 5,540,664; 5,665,071, 5,695,472 and WO/2005/087297 (each of which are incorporated herein by reference for such disclosure) are known. In general, all automatic injectors contain a volume of solution that includes a compound (i.e., a cyclohexenone compound described herein) to be injected. In general, automatic injectors include a reservoir for holding the solution, which is in fluid communication with a needle for delivering the drug, as well as a mechanism for automatically deploying the needle, inserting the needle into the patient and delivering the dose into the patient. Exemplary injectors provide about 0.3 mL, 0.6 mL, 1.0 mL or other suitable volume of solution at about a concentration of 0.5 mg to 50 mg of a compound (i.e., a cyclohexenone compound described herein) per 1 mL of solution. Each injector is capable of delivering only one dose of the compound.

In still other embodiments, the compounds (i.e., cyclohexenone compounds described herein) are administered topically. The compounds described herein are formulated into a variety of topically administrable compositions, such as solutions, suspensions, lotions, gels, pastes, medicated sticks, balms, creams or ointments. Such pharmaceutical compositions optionally contain solubilizers, stabilizers, tonicity enhancing agents, buffers and preservatives.

In yet other embodiments, the compounds (i.e., cyclohexenone compounds described herein) are formulated for transdermal administration. In specific embodiments, transdermal formulations employ transdermal delivery devices and transdermal delivery patches and can be lipophilic emulsions or buffered, aqueous solutions, dissolved and/or dispersed in a polymer or an adhesive. In various embodiments, such patches are constructed for continuous, pulsatile, or on demand delivery of pharmaceutical agents. In additional embodiments, the transdermal delivery of a compound (i.e., a cyclohexenone compound described herein) is accomplished by means of iontophoretic patches and the like. In certain embodiments, transdermal patches provide controlled delivery of a compound (i.e., a cyclohexenone compound described herein). In specific embodiments, the rate of absorption is slowed by using rate-controlling membranes or by trapping the compound within a polymer matrix or gel. In alternative embodiments, absorption enhancers are used to increase absorption. Absorption enhancers or carriers include absorbable pharmaceutically acceptable solvents that assist passage through the skin. For example, in one embodiment, transdermal devices are in the form of a bandage comprising a backing member, a reservoir containing the compound optionally with carriers, optionally a rate controlling barrier to deliver the compound to the skin of the host at a controlled and predetermined rate over a prolonged period of time, and means to secure the device to the skin.

Transdermal formulations described herein may be administered using a variety of devices which have been described in the art. For example, such devices include, but are not limited to, U.S. Pat. Nos. 3,598,122, 3,598,123, 3,710,795, 3,731,683, 3,742,951, 3,814,097, 3,921,636, 3,972,995, 3,993,072, 3,993,073, 3,996,934, 4,031,894, 4,060,084, 4,069,307, 4,077,407, 4,201,211, 4,230,105, 4,292,299, 4,292,303, 5,336,168, 5,665,378, 5,837,280, 5,869,090, 6,923,983, 6,929,801 and 6,946,144.

The transdermal dosage forms described herein may incorporate certain pharmaceutically acceptable excipients which are conventional in the art. In one embodiment, the transdermal formulations described herein include at least three components: (1) a formulation of a compound (i.e., a cyclohexenone compound described herein); (2) a penetration enhancer; and (3) an aqueous adjuvant. In addition, transdermal formulations can include additional components such as, but not limited to, gelling agents, creams and ointment bases, and the like. In some embodiments, the transdermal formulations further include a woven or non-woven backing material to enhance absorption and prevent the removal of the transdermal formulation from the skin. In other embodiments, the transdermal formulations described herein maintain a saturated or supersaturated state to promote diffusion into the skin.

In other embodiments, the compounds (i.e., cyclohexenone compounds described herein) are formulated for administration by inhalation. Various forms suitable for administration by inhalation include, but are not limited to, aerosols, mists or powders. Pharmaceutical compositions of a compound (i.e., a cyclohexenone compound described herein) are conveniently delivered in the form of an aerosol spray presentation from pressurized packs or a nebuliser, with the use of a suitable propellant (e.g., dichlorodifluoromethane, trichlorofluoromethane, dichlorotetrafluoroethane, carbon dioxide or other suitable gas). In specific embodiments, the dosage unit of a pressurized aerosol is determined by providing a valve to deliver a metered amount. In certain embodiments, capsules and cartridges of, such as, by way of example only, gelatins for use in an inhaler or insufflator are formulated containing a powder mix of the compound and a suitable powder base such as lactose or starch.

Intranasal formulations are known in the art and are described in, for example, U.S. Pat. Nos. 4,476,116, 5,116,817 and 6,391,452, each of which is specifically incorporated herein by reference. Formulations, which include a compound (i.e., a cyclohexenone compound described herein), which are prepared according to these and other techniques well-known in the art are prepared as solutions in saline, employing benzyl alcohol or other suitable preservatives, fluorocarbons, and/or other solubilizing or dispersing agents known in the art. See, for example, Ansel, H. C. et al., Pharmaceutical Dosage Forms and Drug Delivery Systems, Sixth Ed. (1995). Preferably these compositions and formulations are prepared with suitable nontoxic pharmaceutically acceptable ingredients. These ingredients are found in sources such as REMINGTON: THE SCIENCE AND PRACTICE OF PHARMACY, 21st edition, 2005, a standard reference in the field. The choice of suitable carriers is highly dependent upon the exact nature of the nasal dosage form desired, e.g., solutions, suspensions, ointments, or gels. Nasal dosage forms generally contain large amounts of water in addition to the active ingredient. Minor amounts of other ingredients such as pH adjusters, emulsifiers or dispersing agents, preservatives, surfactants, gelling agents, or buffering and other stabilizing and solubilizing agents may also be present. Preferably, the nasal dosage form should be isotonic with nasal secretions.

For administration by inhalation, the compounds described herein, may be in a form as an aerosol, a mist or a powder. Pharmaceutical compositions described herein are conveniently delivered in the form of an aerosol spray presentation from pressurized packs or a nebuliser, with the use of a suitable propellant, e.g., dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount. Capsules and cartridges of, such as, by way of example only, gelatin for use in an inhaler or insufflator may be formulated containing a powder mix of the compound described herein and a suitable powder base such as lactose or starch.

In still other embodiments, the compounds (i.e., cyclohexenone compounds described herein) are formulated in rectal compositions such as enemas, rectal gels, rectal foams, rectal aerosols, suppositories, jelly suppositories, or retention enemas, containing conventional suppository bases such as cocoa butter or other glycerides, as well as synthetic polymers such as polyvinylpyrrolidone, PEG, and the like. In suppository forms of the compositions, a low-melting wax such as, but not limited to, a mixture of fatty acid glycerides, optionally in combination with cocoa butter is first melted.

In certain embodiments, pharmaceutical compositions are formulated in any conventional manner using one or more physiologically acceptable carriers comprising excipients and auxiliaries which facilitate processing of the active compounds into preparations which can be used pharmaceutically. Proper formulation is dependent upon the route of administration chosen. Any pharmaceutically acceptable techniques, carriers, and excipients is optionally used as suitable and as understood in the art. Pharmaceutical compositions comprising a compound (i.e., a cyclohexenone compound described herein) may be manufactured in a conventional manner, such as, by way of example only, by means of conventional mixing, dissolving, granulating, dragee-making, levigating, emulsifying, encapsulating, entrapping or compression processes.

Pharmaceutical compositions include at least one pharmaceutically acceptable carrier, diluent or excipient and at least one compound (i.e., cyclohexenone compounds described herein) described herein as an active ingredient. The active ingredient is in free-acid or free-base form, or in a pharmaceutically acceptable salt form. In addition, the methods and pharmaceutical compositions described herein include the use crystalline forms (also known as polymorphs), as well as active metabolites of these compounds having the same type of activity. All tautomers of the compounds described herein are included within the scope of the compounds presented herein. Additionally, the compounds described herein encompass unsolvated as well as solvated forms with pharmaceutically acceptable solvents such as water, ethanol, and the like. The solvated forms of the compounds presented herein are also considered to be disclosed herein. In addition, the pharmaceutical compositions optionally include other medicinal or pharmaceutical agents, carriers, adjuvants, such as preserving, stabilizing, wetting or emulsifying agents, solution promoters, salts for regulating the osmotic pressure, buffers, and/or other therapeutically valuable substances.

Methods for the preparation of compositions comprising the compounds described herein include formulating the compounds with one or more inert, pharmaceutically acceptable excipients or carriers to form a solid, semi-solid or liquid. Solid compositions include, but are not limited to, powders, tablets, dispersible granules, capsules, cachets, and suppositories. Liquid compositions include solutions in which a compound is dissolved, emulsions comprising a compound, or a solution containing liposomes, micelles, or nanoparticles comprising a compound as disclosed herein. Semi-solid compositions include, but are not limited to, gels, suspensions and creams. The form of the pharmaceutical compositions described herein include liquid solutions or suspensions, solid forms suitable for solution or suspension in a liquid prior to use, or as emulsions. These compositions also optionally contain minor amounts of nontoxic, auxiliary substances, such as wetting or emulsifying agents, pH buffering agents, and so forth.

In some embodiments, pharmaceutical composition comprising at least compound (i.e., cyclohexenone compounds described herein) illustratively takes the form of a liquid where the agents are present in solution, in suspension or both. Typically when the composition is administered as a solution or suspension a first portion of the agent is present in solution and a second portion of the agent is present in particulate form, in suspension in a liquid matrix. In some embodiments, a liquid composition includes a gel formulation. In other embodiments, the liquid composition is aqueous.

In certain embodiments, pharmaceutical aqueous suspensions include one or more polymers as suspending agents. Polymers include water-soluble polymers such as cellulosic polymers, e.g., hydroxypropyl methylcellulose, and water-insoluble polymers such as cross-linked carboxyl-containing polymers. Certain pharmaceutical compositions described herein include a mucoadhesive polymer, selected from, for example, carboxymethylcellulose, carbomer (acrylic acid polymer), poly(methylmethacrylate), polyacrylamide, polycarbophil, acrylic acid/butyl acrylate copolymer, sodium alginate and dextran.

Pharmaceutical compositions also, optionally include solubilizing agents to aid in the solubility of a compound (i.e., cyclohexenone compounds described herein). The term "solubilizing agent" generally includes agents that result in formation of a micellar solution or a true solution of the agent. Certain acceptable nonionic surfactants, for example polysorbate 80, are useful as solubilizing agents, as can ophthalmically acceptable glycols, polyglycols, e.g., polyethylene glycol 400, and glycol ethers.

Furthermore, pharmaceutical compositions optionally include one or more pH adjusting agents or buffering agents, including acids such as acetic, boric, citric, lactic, phosphoric and hydrochloric acids; bases such as sodium hydroxide, sodium phosphate, sodium borate, sodium citrate, sodium acetate, sodium lactate and tris-hydroxymethylaminomethane; and buffers such as citrate/dextrose, sodium bicarbonate and ammonium chloride. Such acids, bases and buffers are included in an amount required to maintain pH of the composition in an acceptable range.

Additionally, pharmaceutical compositions optionally include one or more salts in an amount required to bring osmolality of the composition into an acceptable range. Such salts include those having sodium, potassium or ammonium cations and chloride, citrate, ascorbate, borate, phosphate, bicarbonate, sulfate, thiosulfate or bisulfite anions; suitable salts include sodium chloride, potassium chloride, sodium thiosulfate, sodium bisulfite and ammonium sulfate.

Other pharmaceutical compositions optionally include one or more preservatives to inhibit microbial activity. Suitable preservatives include mercury-containing substances such as merfen and thiomersal; stabilized chlorine dioxide; and quaternary ammonium compounds such as benzalkonium chloride, cetyltrimethylammonium bromide and cetylpyridinium chloride.

Still other pharmaceutical compositions include one or more surfactants to enhance physical stability or for other purposes. Suitable nonionic surfactants include polyoxyethylene fatty acid glycerides and vegetable oils, e.g., polyoxyethylene (60) hydrogenated castor oil; and polyoxyethylene alkylethers and alkylphenyl ethers, e.g., octoxynol 10, octoxynol 40.

Still other pharmaceutical compositions may include one or more antioxidants to enhance chemical stability where required. Suitable antioxidants include, by way of example only, ascorbic acid and sodium metabisulfite.

In certain embodiments, pharmaceutical aqueous suspension compositions are packaged in single-dose non-reclosable containers. Alternatively, multiple-dose reclosable containers are used, in which case it is typical to include a preservative in the composition.

In alternative embodiments, other delivery systems for hydrophobic pharmaceutical compounds are employed. Liposomes and emulsions are examples of delivery vehicles or carriers herein. In certain embodiments, organic solvents such as N-methylpyrrolidone are also employed. In additional embodiments, the compounds described herein are delivered using a sustained-release system, such as semipermeable matrices of solid hydrophobic polymers containing the therapeutic agent. Various sustained-release materials are useful herein. In some embodiments, sustained-release capsules release the compounds for a few hours up to over 24 hours. Depending on the chemical nature and the biological stability of the therapeutic reagent, additional strategies for protein stabilization may be employed.

In certain embodiments, the formulations described herein include one or more antioxidants, metal chelating agents, thiol containing compounds and/or other general stabilizing agents. Examples of such stabilizing agents, include, but are not limited to: (a) about 0.5% to about 2% w/v glycerol, (b) about 0.1% to about 1% w/v methionine, (c) about 0.1% to about 2% w/v monothioglycerol, (d) about 1 mM to about 10 mM EDTA, (e) about 0.01% to about 2% w/v ascorbic acid, (f) 0.003% to about 0.02% w/v polysorbate 80, (g) 0.001% to about 0.05% w/v. polysorbate 20, (h) arginine, (i) heparin, (j) dextran sulfate, (k) cyclodextrins, (l) pentosan polysulfate and other heparinoids, (m) divalent cations such as magnesium and zinc; or (n) combinations thereof.

Combination Treatments

In general, the compositions described herein and, in embodiments where combinational therapy is employed based on the mode of action described herein, other agents do not have to be administered in the same pharmaceutical composition, and in some embodiments, because of different physical and chemical characteristics, are administered by different routes. In some embodiments, the initial administration is made according to established protocols, and then, based upon the observed effects, the dosage, modes of administration and times of administration is modified by the skilled clinician.

In some embodiments, therapeutically-effective dosages vary when the drugs are used in treatment combinations. Combination treatment further includes periodic treatments that start and stop at various times to assist with the clinical management of the patient. For combination therapies described herein, dosages of the co-administered compounds vary depending on the type of co-drug employed, on the specific drug employed, on the disease, disorder, or condition being treated and so forth.

It is understood that in some embodiments, the dosage regimen to treat, prevent, or ameliorate the condition(s) for which relief is sought, is modified in accordance with a variety of factors. These factors include the disorder from which the subject suffers, as well as the age, weight, sex, diet, and medical condition of the subject. Thus, in other embodiments, the dosage regimen actually employed varies widely and therefore deviates from the dosage regimens set forth herein. Combinations of compounds (i.e., the cyclohexenone compound described herein) with other AD therapeutic agents are intended to be covered. The combinations of the cyclohexenone compounds and other AD therapeutic agents described herein encompass additional therapies and treatment regimens with other agents in some embodiments. Such additional therapies and treatment regimens can include another AD therapy in some embodiments. Alternatively, in other embodiments, additional therapies and treatment regimens include other agents used to treat adjunct conditions associated with AD or a side effect from such agent in the combination therapy. In further embodiments, adjuvants or enhancers are administered with a combination therapy described herein.

In some embodiments provide compositions for treating or reducing the symptoms of AD comprising a therapeutically effective amount of a cyclohexenone compound having the structure:

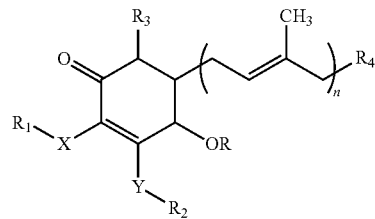

wherein each of X and Y independently is oxygen, $NR_5$ or sulfur;
R is a hydrogen or $C(=O)C_1-C_8$alkyl;
each of $R_1$, $R_2$ and $R_3$ independently is a hydrogen, optionally substituted methyl or $(CH_2)_m-CH_3$;
$R_4$ is $NR_5R_6$, $OR_5$, $OC(=O)R_7$, $C(=O)OR_5$, $C(=O)R_5$, $C(=O)NR_5R_6$, halogen, 5 or 6-membered lactone, $C_1-C_8$alkyl, $C_2-C_8$alkenyl, $C_2-C_8$alkynyl, aryl, glucosyl, wherein the 5 or 6-membered lactone, $C_1-C_8$alkyl, $C_2-C_8$alkenyl, $C_2-C_8$alkynyl, aryl, and glucosyl are optionally substituted with one or more substituents selected from $NR_5R_6$, $OR_5$, $OC(=O)R_7$, $C(=O)OR_5$, $C(=O)R_5$, $C(=O)NR_5R_6$, $C_1-C_8$ alkyl, $C_2-C_8$ alkenyl, $C_2-C_8$ alkynyl, $C_3-C_8$ cycloalkyl, and $C_1-C_8$ haloalkyl;
each of $R_5$ and $R_6$ is independently a hydrogen or $C_1-C_8$alkyl;
$R_7$ is a $C_1-C_8$alkyl, $OR_5$ or $NR_5R_6$;
m=1-12; and n=1-12; or a pharmaceutically acceptable salt, metabolite, solvate or prodrug thereof; and one or more AD therapeutic agents.

EXAMPLES

Example 1: Preparation of the Exemplary Cyclohexenone Compounds

One hundred grams of mycelia from *Antrodia camphorata* were placed into a flask. A proper amount of water and alcohol (70-100% alcohol solution) was added into the flask and were stirred at 20-25° C. for at least 1 hour. The solution was filtered through a filter and 0.45 μm membrane and the filtrate was collected as the extract. In some instances, for example, the extracts were prepared by a solid-state fermented mycelium conditions and compositions disclosed in Lee, T-H., et al., Planta Med 2007; 73:1412-1415.

The filtrate of *Antrodia camphorata* was subjected to High Performance Liquid Chromatography (HPLC) analysis. The separation was performed on a RP18 column, the mobile phase consisted of methanol (A) and 0.3% acetic acid (B), with the gradient conditions of 0-10 min in 95%-20% B, 10-20 min in 20%-10% B, 20-35 min in 10%-10% B, 35-40 min in 10%-95% B, at the flow rate of 1 ml/min. The column effluent was monitored with a UV-visible detector.

The fractions collected at 21.2 to 21.4 min were collected and concentrated to yield compound 5, a product of pale yellow liquid. Compound 5 was analyzed to be 4-hydroxy-5-(11-hydroxy-3,7,11-trimethyldodeca-2,6-dienyl)-2,3-dimethoxy-6-methylcyclohex-2-enone with molecular weight of 408 (Molecular formula: $C_{24}H_{40}O_5$). $^1$H-NMR (CDCl$_3$) δ (ppm)=1.21, 1.36, 1.67, 1.71, 1.75, 1.94, 2.03, 2.07, 2.22, 2.25, 3.68, 4.05, 5.71 and 5.56. $^{13}$C-NMR (CDCl$_3$) δ(ppm): 12.31, 16.1, 16.12, 17.67, 25.67, 26.44, 26.74, 27.00, 30.10, 40.27, 43.34, 59.22, 60.59, 71.8, 120.97, 123.84, 124.30, 131.32, 134.61, 135.92, 138.05, 160.45, and 197.11.

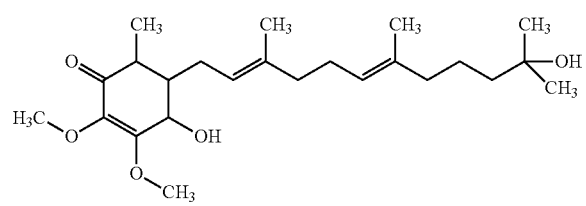

Compound 5: 4-hydroxy-5-(11-hydroxy-3,7,11-trimethyldodeca-2,6-dienyl)-2,3-dimethoxy-6-methylcyclohex-2-enone The fractions collected at 23.7 to 24.0 min were collected and concentrated to yield compound 7, a product of pale yellow liquid. Compound 7 was analyzed to be 4-hydroxy-2,3-dimethoxy-5-(11-methoxy-3,7,11-trimethyldodeca-2,6-dienyl)-6-methylcyclohex-2-enone with molecular weight of 422 (C$_{25}$H$_{42}$O$_5$). $^1$H-NMR (CDCl$_3$) δ (ppm)=1.21, 1.36, 1.71, 1.75, 1.94, 2.03, 2.07, 2.22, 2.25, 3.24, 3.68, 4.05, 5.12, 5.50, and 5.61. $^{13}$C-NMR (CDCl$_3$) δ (ppm): 12.31, 16.1, 16.12, 17.67, 24.44, 26.44, 26.74, 27.00, 37.81, 39.81, 40.27, 43.34, 49.00, 59.22, 60.59, 120.97, 123.84, 124.30, 135.92, 138.05, 160.45 and 197.12.

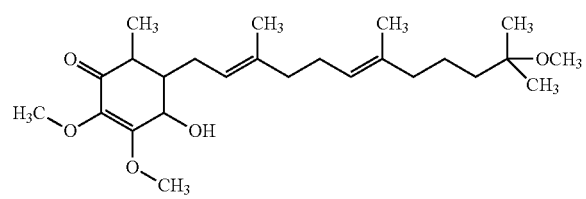

Compound 7: 4-hydroxy-2,3-dimethoxy-5-(11-methoxy-3,7,11-trimethyldodeca-2,6-dienyl)-6-methylcyclohex-2-enone The fractions collected at 25 to 30 min were collected and concentrated to yield 4-hydroxy-2,3-dimethoxy-6-methyl-5-(3,7,11-trimethyldodeca-2,6,10-trienyl)cyclohex-2-enone (compound 1), a product of pale yellow brown liquid. The analysis of compound 1 showed the molecular formula of C$_{24}$H$_{38}$O$_4$, molecular weight of 390 with melting point of 48 to 52° C. NMR spectra showed that $^1$H-NMR (CDCl$_3$) δ (ppm)=1.51, 1.67, 1.71, 1.75, 1.94, 2.03, 2.07, 2.22, 2.25, 3.68, 4.05, 5.07, and 5.14; $^{13}$C-NMR (CDCl$_3$) δ (ppm)= 12.31, 16.1, 16.12, 17.67, 25.67, 26.44, 26.74, 27.00, 39.71, 39.81, 40.27, 43.34, 59.22, 60.59, 120.97, 123.84, 124.30, 131.32, 135.35, 135.92, 138.05, 160.45, and 197.12.

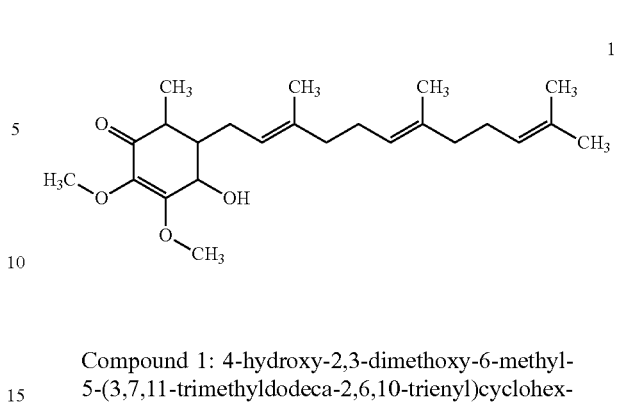

Compound 1: 4-hydroxy-2,3-dimethoxy-6-methyl-5-(3,7,11-trimethyldodeca-2,6,10-trienyl)cyclohex-2-enone Compound 27, a metabolite of compound 1, was obtained from urine samples of rats fed with Compound 1 in the animal study. Compound 27 was determined to be 4-hydroxy-2,3-dimethoxy-6-methyl-5-(3-methyl-2-hexenoic acid)cyclohex-2-enone with molecular weight of 312 (C$_{16}$H$_{24}$O$_6$). Compound 25 which was determined as 2,3-dimethoxy-5-methyl-6-((2E,6E)-3,7,11-trimethyldodeca-2,6,10-trienyl)cyclohexa-2,5-diene-1,4-dione (molecular weight of 386.52, C$_{24}$H$_{34}$O$_4$), was obtained from the purification process.

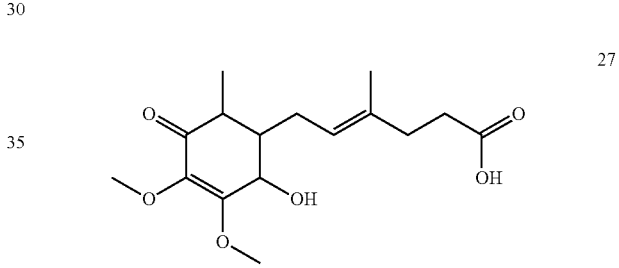

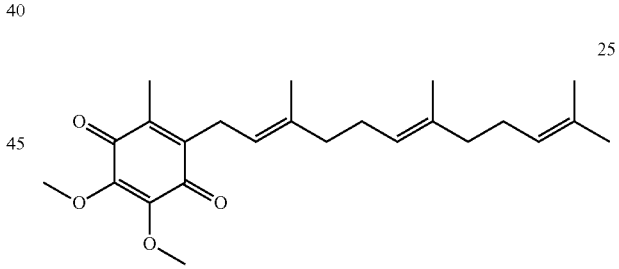

Compound 26, 4-hydroxy-2-methoxy-6-methyl-5-((2E,6E)-3,7,11-trimethyldodeca-2,6,10-trienyl)cyclohex-2-enone, was also prepared by purification process with molecular weight of 350.53 (C$_{23}$H$_{36}$O$_3$). Compound 28 was also prepared.

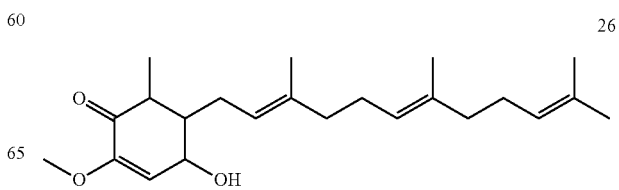

28

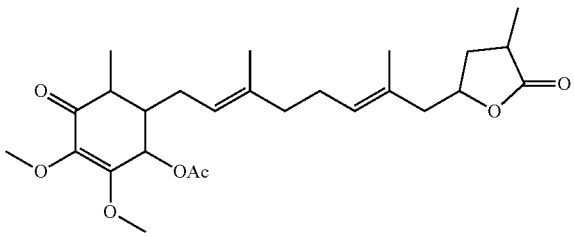

Alternatively, the exemplary compounds may be prepared from 4-hydroxy-2,3-dimethoxy-6-methylcyclohexa-2,5-dienone, or the like. See for example, see examples from U.S. Pat. No. 9,365,481 and U.S. patent publication No. 2016-0237012. Similarly, other cyclohexenone compounds having the structure

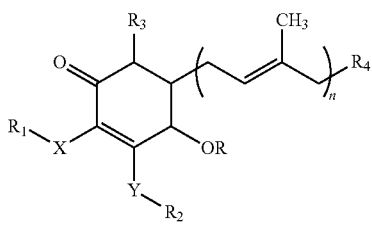

are isolated from *Antrodia camphorata* or prepared synthetically or semi-synthetically from the suitable starting materials. An ordinary skilled in the art would readily utilize appropriate conditions for such synthesis.

Example 2: Outside-in Animal Model Study

BALC/c female rat in 6-8-week old is used. Each group has 6-8 rats. Blood sample was taken from the cheek of rat before sensitization. On day 1 and day 8, mice were injected intraperitoneally with 50 μg/mice of OVA-aluminum hydroxide (1:1 v/v). The mice were epicutaneously sensitized with OVA patches on day 15. OVA (100 μg) prepared in PBS was contained in a 2×2-cm patch of sterile gauze that was placed on the shaved backs of mice and secured to the skin with 3 M Tegader film followed by 3 M Coban tape to secure the gauze. After 3 days, the gauze was removed and reapplied. The procedure was repeated three times. Day 27, all the mice in the study was sacrificed and examined.

Schedule: Group blank N: blank.

Group sensitization O:

days 1 and 8 were injected OVA (sensitization), day 15 applied OVA gauze for 3 days (challenge) and rested one day. The application of OVA gauze procedure was repeated 3 times. Starting on day 14, the mice in the group were fed water.

Group L:

Same procedure as group O except the mice were fed low dose (5 mg/kg BW) of exemplary compound 1.

Group M:

Same procedure as group O except the mice were fed medium dose (15 mg/kg BW) of exemplary compound 1.

Group H:

Same procedure as group O except the mice were fed high dose (45 mg/kg BW) of exemplary compound 1.

The procedure is summarized in the following table.

| Group | Notation | Sensitization (IP) | Challenge | Treat |
|---|---|---|---|---|
| N | Native | — | — | — |
| O | OVA | OVA 50 μg | OVA 100 μg | water |
| L | Low | OVA 50 μg | OVA 100 μg | 5 mg/Kg BW |
| M | Medium | OVA 50 μg | OVA 100 μg | 15 mg/Kg BW |
| H | High | OVA 50 μg | OVA 100 μg | 45 mg/Kg BW |

Example 3: Skin Surface Study and Tissue Section

For histological examination, skin specimens (0.5×0.5 cm) were obtained and taken photos (see FIG. 2A-E) from patched dorsal skins of the mice after the mice were sacrificed. The blood samples were taken from the mice as well. The muscle layer and the fat layer of the skin specimens were separated. The skin specimens were fixed with 10% formalin in neutral buffered solution in a 6-well disk and embedded in paraffin after drying.

Serum Immunoglobulin Analysis.

The measurement was employed by sandwich-ELISA. A proper amount of anti-mice IgE antibody was prepared in a 96 well Nunc-Immuno plate with a coating buffer (pH 9.6). After overnight at 4° C., the plates were washed with PBST buffer to remove unconjugated antibody, then blocked with 200 μl/well blocking buffer (1% BSA/PBS) at room temperature for 30 min. The plates were then washed with PBST buffer, and added of 100 μl of the 50 folds diluted mice serums or the IgG, IgA, IgE standard references with known concentration.

The test solution or the IgE standard contained wells were reacted at room temperature for one hour and washed with PBST buffer, and added 100 μl/well of the proper concentrated HRP conjugated anti-IgE secondary antibody. The plates were reacted at room temperature for one hour and then wished with PBST buffer and then reacted with TMB substrate. After 5 min, the reaction was stopped with 100 μl 2N $HSO_4$ and then measured at 450 nm wavelength to determine the absorption value. The value was used to determine the antibody concentration in serum.

Delayed Allergic Reactions.

OVA was injected into abdominal cavity of the mice. After 6 days, OVA was applied to the right hind limb of the mice via subcutaneous injection, or to the inside and outside ears of the mice. After 24 hours of application, the swelling thickness of the hind limb, or the ears were measured against ones without application (i.e., control group) as the basis of the delayed allergic reaction.

Determination of Skin Physiology.

After anesthesia, the skins of the mice were measured trans-epidermal water loss, and relative humidity by Tewameter TM210. The skin pH was measured as well. See FIG. 3A-3C.

Collection of the Mice Spleen Cells.

The spleens of the mice were aseptically removed and put into RPMI medium (10% FBS). Using the barrel from a 20 mL syringe to grind spleens. The resulted spleen suspension was poured through a sterile metal cell-strainer (70 μm) and centrifuged at 300×g for 5 minutes at 4° C. The supernatant was removed and the pellet was dissolved in 5 ml RBC lysis buffer. The solution was cooled down by ice for 10 minutes and then added the same volume of cRPMI medium to stop reaction. The resulted suspension was centrifuged at 300×g for 5 minutes at 4° C. The supernatant was removed and the pellet was dissolved in 10 ml cRPMI medium and then the cell numbers were counted. The concentration of the resulted solution was adjusted to 1×10⁶/ml with cRPMI medium. The resulted cells seeded placed to a 12-wells disk and added 50 µg/ml OVA, 5 µg/ml ConA and 10 µg/ml PHA-L to each well. Each well was challenged for 72 hours and then centrifuged at 300×g for 5 minutes at 4° C. The supernatants of each well were collected and stored at −80° C.

Collection of the Mice Lymph Nodes.

The lymph nodes of the mice were aseptically removed and put into RPMI medium (10% FBS). Using the barrel from a 20 mL syringe to grind lymph nodes. The resulted suspension was poured through a sterile metal cell-strainer (70 µm) and centrifuged at 300×g for 5 minutes at 4° C. The supernatant was removed and the pellet was dissolved in 5 ml RBC lysis buffer. The solution was cooled down by ice for 10 minutes and then added the same volume of cRPMI medium to stop reaction. The resulted suspension was centrifuged at 300×g for 5 minutes at 4° C. The supernatant was removed and the pellet was dissolved in 10 ml cRPMI medium and then the cell numbers were counted. The concentration of the resulted solution was adjusted to 1×10⁶/ml with cRPMI medium. The resulted cells were seeded to a 12 wells disk and added 50 µg/ml OVA, 5 µg/ml ConA and 10 µg/ml PHA-L to each well. Each well was challenged for 72 hours and then centrifuged at 300×g for 5 minutes at 4° C. The supernatants of each well were collected and stored at −80° C.

Quantitation of cytokine production is a valuable adjunct to standard immunologic assays in defining several pathologic processes. Measurement of cytokine levels has yielded useful information on the pathologic process in AD.

Cytokine Secretion Test.

Adjusted concentration of the isolated lymphocytes to 1×10⁶/ml and placed into a 24-well plate. The plate was subject to the quantified PHA, ConA or OVA to stimulate spleen cells or lymphocytes. The disk was cultured for 24 or 72 hours, and the supernatants of each well were collected to measure the amount of cytokine secretion. The cytokine was measured by sandwich-ELISA. The ELISA plate was processed to apply antibody and incubate overnight at 4° C. The plate was washed with 1% PBS-BSA before the test. The specimens were added to the plate and kept at room temperature for 2 hours and then biotin linked anti-cytokine antibodies were added. After two hours at room temperature, the plate was added avidin-linked peroxidase. After another two hours, TMB was used for enzyme/substrate readout. Color development was measured at 450 nm using an automated microplate ELISA reader. The concentration of each reagent used in the above procedure should be determined before test by referencing with a lymphatic media with the known concentration.

Skin Keratinocyte Apoptosis.

The skin specimens were cut from the mice. The muscle layer and the fat layer of the skin specimens were discarded and then put the skin into a PBS containing 10% antibiotic for 5 minute. The skin specimens were then taken out and put into a solution o 0.25% trypsin at 37° C. for 30 minutes. The skin specimens were taken out and put on a 10 cm disk. The skin keratinocytes were scraped out with a blade and then wash with trypsin, centrifuged, re-suspended the pellet in PBS to a concentration of 2×10⁵/ml. Fluorescein isothiocyanate (FITC) and phycoerythin (PE) conjugated antibodies were used in Fluorescence-activated cell sorting (FACS) analysis to determine (a) apoptotic status of epidermal keratinocytes.

Statistical Analysis

Results of the Examples were expressed as the mean±SEM and analyzed by unpaired t-test. A two-tailed P-value of less than 0.05 was considered significant. Results As shown in FIG. 1, all mice administration of oral doses of compound 1 did not lead to any loss in body weight or any observed clinical signs through the study period, and the body weight change was no significant difference between all treatment groups.

As shown in FIG. 2A-E, the mice in Group O shows more severe swelling and inflammation than the mice in Group N. There was no significant difference between the low dose Group L and the medium dose Group M compared to Group O. It is worth noting that the skin conditions of the mice in Group H (high dose of Compound 1) are better compared to the mice in Group O, with less swelling and inflammatory condition. The skins are more smooth as well. Thus, it is clear that the mice fed with high dose of exemplary compound 1 had improved AD conditions.

As indicated by Transepidermal Waterloss (TEWL), when the value of TEWL is smaller, the less loss of water from the skin surface, which means the better condition of the protective layer of the epidermis. When the TEWL value is larger, the more severe damage to the epidermal protective layer as the water loss is more.

As shown in FIG. 3A, before day 14 when the dorsal skins of the mice were applied OVA patches, the TEWL values of each group are very similar. On day 27, the TEWL value of Group O is significantly higher than the value of Group N, which indicates OVA induced AD causing water loss from the skin surfaces. The TEWL values from Group L, Group M, and Group H are statically significant lower compared with Group O, which indicates the improvement of the epidermal damage in these groups. The data also shows the improvement is dose dependent with the higher dosage to provide better improvement.

As indicated by relative humidity (RH), when the RH value is smaller, it means that the skin has better water retention and the skin structure is sounder. When the RH value is larger, it means that the skin is dryer and the skin structure is less perfect.

As shown in FIG. 3B, before day 14 when the dorsal skins of the mice were applied OVA patches, the RH values of each group are very similar. On day 27, the RH value of Group O is statistically significantly higher than the value of Group N, which indicates OVA induced AD resulting a dry skin and skin structure damages. The RH values from Group L, Group M, and Group H are statically significant lower compared with Group O, which indicates the improvement of the epidermal damage in these groups. The data also shows the improvement is dose dependent with the higher dosage to provide better improvement.

As shown in FIG. 3C, on day 14 when the dorsal skins of the mice were applied OVA patches and on day 27, the pH values of each group are very similar.

Thus, by taking an effective amount of an exemplary compound, the skin physiological function reactions in AD can be improved as evidenced by the results of TEWL and RH values.

Hematoxylin and eosin stain or haematoxylin and eosin stain (H&E stain or HE stain) is one of the principal stains in histology. This staining method is based on the affinity of cellular components for the dyes. The sample structure difference results in staining difference. Hematoxylin stains the basophilic structure to blue-violet, while hematin stains eosinophilic structures to red, pink, or orange.

As shown in FIG. 4A-E, the H&E stain results indicated that—both epidermis and dermis layers of the skin specimens in Group O were significantly thickened when compared with Group N. The layers also show increase numbers of inflammatory cell infiltration. The epidermis and dermis layers in Group L, Group M, and Group H were significantly thinner and had reduced infiltration of the inflammatory cells compared with the results of Group O.

Particularly, as shown in FIGS. 4F and 4G, the epidermis and dermis layers of Group O is statistically significantly thicker than the ones of Group N, which indicates OVA induced a large number infiltration of inflammatory cells resulting thicker layers. The epidermis and dermis layers in Group L, Group M, and Group H are statically significant less thickness compared with Group O. The data also shows the decrease in thickness of the epidermis and dermis in a dose-dependent manner.

Thus, by taking an effective amount of an exemplary compound, the skin epidermis condition in AD can be improved as evidenced by the results of H&E-stained skin specimens.

Eosinophils (eosinophilic leukocytes) are granulocytes that develop during hematopoiesis in the bone marrow before migrating into blood. They are largely generated during inflammation and parasites infections. They have been shown to be useful for monitoring a variety of active inflammatory diseases including bronchial asthma, atopic dermatitis, rhinitis, allergic ophthalmia, allergic otitis, parasitic and bacterial infections, autoimmune diseases, and chronic burnout.

As shown in FIG. 5A-E, compared Group O eosinophils stain results with Group N, eosinophils in the dermis of the skin specimens in Group O were significantly increased. Eosinophils in the dermis of Group L, Group M, and Group H were significantly decreased in comparison with the results of Group O.

FIG. 5F shows the results of the cell number counts of eosinophils in dermis.

The number of eosinophils cells in dermis of Group O is statistically significantly increased than that of Group N, which indicates OVA induced AD causing the number of eosinophils cells to be increased. The number of eosinophils cells in dermis of Group L, Group M, and Group H were decreased compared with Group O. Especially the number decreased in Group M and Group H is statically significant.

Thus, by taking an effective amount of an exemplary compound, the condition of dermis in AD can be improved as evidenced by the results of eosinophils stained cells.

Atopic dermatitis causes itching sensation because skin damage will activate the epidermis to produce thymus stromal lymphopoietin (Thymic stromal lymphopoietin, TSLP).

As shown in 6A-E, compared Group O TSLP stain results with Group N, TSLP in the dermis of the skin specimens in Group O were significantly increased. TSLP staining in the dermis of Group L, Group M, and Group H were significantly decreased in comparison with the results of Group O.

FIG. 6F shows the quantified cell count results of the TSLP cell staining in epidermis of the mice. The number of TSLP-stained cells in the sensitized Group O was statistically significantly higher than that in Group N, which indicates OVA induced AD causing the number of TSLP-stained cells to be increased.

The number of TSLP-stained cells in epidermis in Group L, Group M, and Group H are lower than that in Group O. Especially the numbers decreased in Group M and Group H are statically significant.

Thus, by taking an effective amount of an exemplary compound, the condition of epidermis in AD can be improved as evidenced by the results of TSLP-stained cells.

Langerhans cells can be used to detect skin barrier conditions. When the skin is damaged, langerhans cells will be secreted in a large number to swallow and destruct (phagocytize) external viruses. Langerhans cells can also stimulate the production of some lymphocytes.

As shown in FIG. 7A-E, providing the langerhans cell staining results, the langerhans cell stained amount in the sensitized Group O was significantly higher than that in Group N. Langerhans staining amounts in Group L, Group M, and Group H were clearly decreased in comparison with the amount in Group O.

FIG. 7F shows the quantified cell count results of the langerhans cell staining. The number of langerhans-stained cells in the sensitized Group O was statistically significantly higher than that in Group N, which indicates OVA induced AD causing the number of langerhans-stained cells to be increased. The number of langerhans-stained cell count in Group L, Group M, and Group H are statically significantly lower than that in Group O.

Thus, by taking an effective amount of an exemplary compound, the skin barrier condition in AD can be improved as evidenced by the results of langerhans-stained cells.

When the body has an allergic reaction, the serum immunoglobulin E (Immunoglobulin E, IgE) will increase.

FIG. 8A shows the total IgE amounts of each group. On day 0, there was no difference among each group. On day 14, before the mice were applied OVA patches on the dorsal skins, except Group N mice, the mice in other groups all had OVA injection into abdominal cavity. The total IgE in Group O, Group L, Group M, and Group H are statically higher than that in Group N, which indicates the OVA injection causing allergic reaction in body. On day 27, the total IgE in Group O was statistically significantly higher than that in Group N, which indicates the successful establishment of AD model by OVA patches to the mice of Group O. The amount of total IgE in Group L, Group M, and Group H are statically significantly lower than that in Group O and the decrease was dose dependent.

FIG. 8B shows the OVA specific IgE amounts On day 0, there was no difference among each group. On day 14, before the mice were applied OVA patches on the dorsal skins, except Group N mice, the mice in other groups all had OVA injection into abdominal cavity. of each group. The OVA specific IgE amounts in Group O, Group L, Group M, and Group H are statically higher than that in Group N, which indicates the OVA injection causing allergic reaction in body. On day 27, the OVA specific IgE in Group O was statistically significantly higher than that in Group N, which indicates the successful establishment of AD model by OVA patches to the mice of Group O. The amounts of OVA specific IgE in Group L, Group M, and Group H were statically significantly lower than that in Group O.

Thus, by taking an effective amount of an exemplary compound, the total IgE and OVA specific IgE in AD can be decreased as evidenced by the results of serum IgE measurements.

As shown in FIG. 9A, on day 27, the ear thickness in the sensitized Group O was not thickened in comparison with that in Group N. The ear thickness in Group L, Group M, and Group H was not different from that in Group O.

As shown in FIG. 9B, the hind limb thickness in Group O was statistically significantly thicker than that in Group N. The hind limb thickness in Group L, Group M, and Group H were clearly less than that in Group O, where one in Group L is statistically significant.

Thus, by taking an effective amount of an exemplary compound, the delayed allergic reactions to ears and legs in atopic dermatitis can be improved.

The Results of Spleen Cell's Hormone Secretion Simulated by PHA, ConA and OVA for 24 Hours.

The mice in each group were sacrificed after day 27 and the spleen cells were collected. The concentration of the spleen cells containing solution was adjusted to $1 \times 10^6$/ml and then subject to 24 hours' stimulation by PHA, ConA and OVA. The amounts of IFN-γ, IL-4, IL-12 and TNF-α generated in spleen cells were measured.

As shown in FIG. 10A, the amounts of IFN-γ secretion after 24 hours' PHA stimulation in Group O and Group N were about the same. The amounts of IFN-γ secretion in Group L, Group M, and Group H were a little bit higher than that in Group O, but has no statistic meaning. In term of the amounts of IFN-γ secretion after 24 hours' ConA stimulation, the amounts of IFN-γ secretion in Group O were statistically significantly lower than one in Group N. The amounts of IFN-γ secretion in Group L, Group M, and Group H were statistically significantly higher than one in Group O. The amounts of IFN-γ secretion after 24 hours' OVA stimulation in each group were about the same without showing differences.

As shown in 10B, the amounts of IL-4 secretion in Group O and Group N after 24 hours' PHA stimulation were about the same. The amounts of IL-4 secretion after 24 hours' ConA stimulation in Group O were statically significantly higher than one in Group N. The amounts of IL-4 secretion in Group L, Group M, and Group H were lower than one in Group O, especially statically significant in Group L and Group M. The amounts of IL-4 secretion after 24 hours' OVA stimulation in each group were about the same without showing any differences.

As shown in FIG. 10C, the amounts of IL-12 secretion in each group after 24 hours' PHA stimulation were about the same. The amounts of IL-12 secretion in Group O after 24 hours' ConA stimulation were a little lower than one in Group N, but has no statistic meaning. The amounts of IL-12 secretion in Group L, Group M, and Group H were higher than that in Group O, especially statically significant in Group L and Group M. The amounts of IL-12 secretion after 24 hours' OVA stimulation in each group were about the same without showing difference.

As shown in FIG. 10D, the amounts of TNF-α secretion in each group after 24 hours' PHA stimulation were about the same. The amounts of TNF-α secretion in Group O after 24 hours' ConA stimulation were statistically significantly higher than one in Group N. The amounts of TNF-α secretion in Group L, Group M, and Group H were statistically significantly lower than that in Group O. The amount of TNF-α secretion after 24 hours' OVA stimulation in Group O was a little bit higher than one in Group N, but has not statistic significance. The amounts of TNF-α secretion in Group L, Group M, and Group H were a little bit lower than that in Group O, but were not statistic significant.

Thus, an effective amount of an exemplary compound can affect the secretion of certain biomarkers from spleen cells in AD.

The Results of Spleen Cell's Hormone Secretion Simulated by PHA, ConA and OVA for 72 Hours.

The mice in each group were sacrificed after day 27. The concentration of the spleen cells containing solution was adjusted to $1 \times 10^6$/ml and then subject to 72 hours' stimulation by PHA, ConA and OVA. The amounts of IFN-γ, IL-4, IL-12 and TNF-α generated in spleen cells were measured.

As shown in FIG. 11A, in term of the amounts of IFN-γ secretion after 72 hours' PHA stimulation in Group O and Group N were about the same. The amounts of IFN-γ secretion in Group L and Group M were about the same as one in Group O. The amount in Group H was a little bit higher than that in Group O, but has no statistic meaning. In term of the amounts of IFN-γ secretion after 72 hours' ConA stimulation, the amount of IFN-γ secretion in Group O was about the same as on in Group N. The amounts of IFN-γ secretion in Group L, Group M, and Group H were a little bit higher than one in Group O, especially one in Group M to be statistically significant. The amounts of IFN-γ secretion after 72 hours' OVA stimulation in in Group O and Group N were about the same. The amounts in Group L and Group M are about the same as one in Group O. The amount in Group H was a little bit higher than one in Group O but without showing statistical meaning.

As shown in 11B, the amounts of IL-4 secretion in Group O and Group N after 72 hours' PHA stimulation were about the same. The amounts of IL-4 secretion after 72 hours' ConA stimulation in Group O were statically significantly higher than one in Group N. The amounts of IL-4 secretion in Group L, Group M, and Group H were statically significantly lower than one in Group O. The amounts of IL-4 secretion after 72 hours' OVA stimulation in each group were about the same without showing any differences.

As shown in FIG. 11C, the amounts of IL-12 secretion in each group after 72 hours' PHA, ConA or OVA stimulation were about the same.

As shown in FIG. 11D, the amounts of TNF-α secretion in each group after 72 hours' PHA stimulation were about the same. The amounts of TNF-α secretion in Group O after 72 hours' ConA stimulation were statistically significantly higher than one in Group N. The amounts of TNF-□ secretion in Group L, Group M, and Group H were statistically significantly lower than that in Group O. The amounts of TNF-α secretion after 72 hours' OVA stimulation in each group are about the same without showing differences.

The Results of Lymphocytes' Cytokine Secretion Simulated by PHA, ConA and OVA for 24 Hours.

The mice in each group were sacrificed after day 27 and the lymphocytes were collected. The concentration of the lymphocytes containing solution was adjusted to $1 \times 10^6$/ml and then subject to 24 hours' stimulation by PHA, ConA and OVA. The amounts of IFN-γ, IL-4, IL-12 and TNF-α generated in lymphocytes were measured.

As shown in FIG. 12A, the amounts of IFN-γ secretion after 24 hours' PHA stimulation in each group were about the same. In term of the amounts of IFN-γ secretion after 24 hours' ConA stimulation, the amounts of IFN-γ secretion in Group O were statistically significantly higher than one in Group N. The amounts of IFN-γ secretion in Group L, Group M, and Group H were statistically significantly higher than one in Group O. The amounts of IFN-γ secretion after 24 hours' OVA stimulation in each group were about the same without showing differences.

As shown in 12B, the amounts of IL-4 secretion in each group after 24 hours' PHA stimulation were about the same. The amounts of IL-4 secretion after 24 hours' ConA stimulation in Group O were statically significantly higher than one in Group N. The amounts of IL-4 secretion in Group L, Group M, and Group H were statistically significantly lower than one in Group O. The amounts of IL-4 secretion after 24 hours' OVA stimulation in each group were about the same without showing any differences.

As shown in FIG. 12C, the amounts of IL-12 secretion in each group after 24 hours' PHA, ConA, or OVA stimulation were about the same.

As shown in FIG. 12D, the amounts of TNF-α secretion in each group after 24 hours' PHA stimulation were about the same. The amounts of TNF-α secretion in Group O after 24 hours' ConA stimulation were statistically significantly higher than one in Group N. The amounts of TNF-α secretion in Group L, Group M, and Group H were statistically significantly lower than that in Group O. The amounts of TNF-α secretion after 24 hours' OVA stimulation in Group in each group were about the same without showing any differences.

The Results of Lymphocytes' Cytokine Secretion Simulated by PHA, ConA and OVA for 72 Hours.

The mice in each group were sacrificed after day 27 and the lymphocytes were collected. The concentration of the lymphocytes containing solution was adjusted to $1 \times 10^6$/ml and then subject to 72 hours' stimulation by PHA, ConA and OVA. The amounts of IFN-γ, IL-4, IL-12 and TNF-α generated in lymphocytes were measured.

As shown in FIG. 13A, the amounts of IFN-γ secretion after 72 hours' PHA stimulation in each group were about the same. In term of the amounts of IFN-γ secretion after 72 hours' ConA stimulation, the amounts of IFN-γ secretion in Group O were about the same as one in Group N. The amounts of IFN-γ secretion in Group L, Group M, and Group H were a little bit higher than one in Group O, but without showing statistic meaning. The amounts of IFN-γ secretion after 72 hours' OVA stimulation in each group were about the same without showing differences.

As shown in 13B, the amounts of IL-4 secretion in each group after 72 hours' PHA stimulation were about the same. The amounts of IL-4 secretion after 72 hours' ConA stimulation in Group O were statically significantly higher than one in Group N. The amounts of IL-4 secretion in Group L, Group M, and Group H were lower than one in Group O, especially ones in Group M and Group H with statistical significance. The amounts of IL-4 secretion after 24 hours' OVA stimulation in each group were about the same without showing any differences.

As shown in FIG. 13C, the amounts of IL-12 secretion in each group after 72 hours' PHA, ConA, or OVA stimulation were about the same.

As shown in FIG. 13D, the amounts of TNF-α secretion in each group after 72 hours' PHA stimulation were about the same. The amounts of TNF-α secretion in Group O after 72 hours' ConA stimulation were statistically significantly higher than one in Group N. The amounts of TNF-α secretion in Group L, Group M, and Group H were statistically significantly lower than that in Group O. The amounts of TNF-α secretion after 24 hours' OVA stimulation in Group in each group were about the same without showing any differences.

Example 4: Clinical Trial Study of Compound 1 for Treating Atopic Dermitis Patients Clinical trial to study the effectiveness of the cyclohexenone compounds described herein such as Compound 1 in treating patients who have atopic dermatitis.

Study Design: A randomized, three-Arms, double-blind, dosing-ranging, placebo-controlled trial.

Primary Purpose: This study will compare the safety and efficacy of Compound 1 (e.g., 50, 100, and 200 mg) to placebo in patients with moderate atopic dermatitis.

Objectives:

Primary Objective: To evaluate the activity of Compound 1 in patients with moderate to severe atopic dermatitis.

Secondary Objective: To assess the mechanism and cytokines change of Antroquinonol in patients with atopic dermatitis.

Exploratory Objective: To explore potential relationships between of Antroquinonol exposure and safety and efficacy endpoints.

OUTLINE: A sample size of 60 patients totally with 20 patients per arm will be enrolled. Patients will receive Antroquinonol 50 mg, 100 mg or placebo per day (QD) on Day 0 for 12 weeks or until documented evidence of unacceptable toxicity, non-compliance or withdrawal of consent by the patient, or the investigator decides to discontinue treatment, whichever comes first. The time of study drug administration should be recorded in the patient diary. Scores assessments will be performed at Screening, Day 0, Day 28, Day 56 and Day 84 including EASI score, SCORAD, sIGA score. The primary endpoint is the percentage improvement between baseline and week 12 in Eczema Area and Severity Index (EAST).

Inclusion Criteria

Ages Eligible for Study: between the ages of 12 and 65 years who had moderate-to-severe atopic dermatitis (using the Hanifin and Rajka Diagnostic Criteria).

Patients with body weight ≥35 kg and ≤120 kg.

To be eligible to participate, patients were required to have
  a. a score of at least 10 on the Eczema Area and Severity Index (EASI), which ranges from 0 to 72, with higher scores indicating worse disease severity;
  b. a score for pruritus of at least 30 mm on a visual-analogue scale, which ranges from 0 (no itch) to 100 mm (worst itch imaginable);
  c. a score of at least 3 on the static Investigator's Global Assessment (sIGA), which ranges from 0 (clear) to 4 (severe disease).
  d. BSA affected or PSAI≥5%

Exclusion Criteria
  1. Patients with active dermatologic diseases concomitant with atopic dermatitis.
  2. Patients with severe medical condition(s) that in the view of the investigator prohibits participation in the study.
  3. Subjects with Netherton's syndrome or other genodermatoses that result in a defective epidermal barrier.
  4. Any subject who is immunocompromised or has a history of malignant disease. This information will be gathered verbally from the patient while taking a medical history from the patient, and will not involve further testing such as an HIV test.
  5. Subjects with a history of psychiatric disease or history of alcohol or drug abuse that would interfere with the ability to comply with the study protocol.
  6. Any noticeable breaks or cracks in the skin on either arm, including severely excoriated skin or skin with open or weeping wounds suggestive of an active infection or increased susceptibility to infection.
  7. Ongoing participation in another investigational trial.
  8. Use of any oral or topical antibiotic for up to four weeks prior to the Treatment visit or active infection that in the opinion of the investigator would compromise the patient's ability to tolerate therapy.
  9. Use of any systemic immunosuppressive therapy (e.g. CsA, MTX, etc.) within four weeks of the Treatment visit.

10. Participant who has a condition or is in a situation that, in the investigator's opinion, may put the patient at significant risk, or may significantly interfere with the patient's participation in the study.
11. Subjects with prosthetic heart valves, pacemakers, intravascular catheters, or other foreign or prosthetic devices.
12. History of food or drug related severe anaphylactoid or anaphylactic reaction(s).
13. Pregnancy or breast feeding.
14. History or presence of epilepsy, significant neurological disorders, cerebrovascular attacks or ischemia.
15. History or presence of myocardial infarction or cardiac arrhythmia which requires drug therapy.
16. Patients who are unable to complete questionnaires on paper.
17. Clinically significant laboratory abnormalities.
18. History of malignancy of any organ system, treated or untreated.

Primary Study Endpoints: The percentage improvement between baseline and week 12 in Eczema Area and Severity Index.

Secondary Study Endpoints: Secondary endpoints at week 12 and at each time point (weeks 4, 8 and 12) included improvement from baseline in the
1. EASI score;
2. Scoring Atopic Dermatitis (SCORAD), which ranges from 0 to 103, with higher scores indicating more severe disease;
3. sIGA score, which ranges from 0 to 4; 4. Body-surface area affected by atopic dermatitis;
5. Pruritus verbal rating scale, which describes pruritus intensity from 0 (none) to 10 (very severe) daily;
6. Sleep-disturbance visual-analogue scale, which ranges from 0 (no sleep disturbance) to 10 (inability to sleep at all) daily;
7. The proportion of patients with 25%, 50%, and 75% improvement in scores on the pruritus visual-analogue scale, EASI, and SCORAD;
8. The proportion of patients with an improvement of at least 2 points on the sIGA and pruritus verbal rating scale.

Other efficacy endpoint: The percentage change between baseline and week 12 in serum cytokines, including TARC/CCL17, IFN-γ, TNF-α, IL-18, IL-6, IL-β.

Example 5: Oral Formulation

To prepare a pharmaceutical composition for oral delivery, equal weight amount of an exemplary Compound 1 was mixed with equal weight amount of corn oil (e.g., 25 mg, 50 mg, 100 mg, 200 mg). The mixture was incorporated into an oral dosage unit in a capsule, which is suitable for oral administration.

In some instances, 100 mg of a compound described herein is mixed with 750 mg of starch. The mixture is incorporated into an oral dosage unit for, such as a hard gelatin capsule, which is suitable for oral administration.

Example 6: Sublingual (Hard Lozenge) Formulation

To prepare a pharmaceutical composition for buccal delivery, such as a hard lozenge, mix one part of a compound described herein, with 4 to 5 parts of powdered sugar mixed, with suitable amount of light corn syrup, distilled water, and mint extract. The mixture is gently blended and poured into a mold to form a lozenge suitable for buccal administration.

Example 7: Inhalation Composition

To prepare a pharmaceutical composition for inhalation delivery, 20 mg of a compound described herein is mixed with 50 mg of anhydrous citric acid and 100 mL of 0.9% sodium chloride solution. The mixture is incorporated into an inhalation delivery unit, such as a nebulizer, which is suitable for inhalation administration.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A method for treating or reducing the symptoms of atopic dermatitis in a subject comprising administering to said subject a therapeutically effective amount of a cyclohexenone compound having the structure:

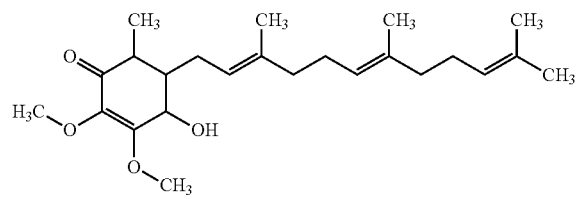 [SMILES: COC1=C(OC)C(O)C(C/C=C(\C)CC/C=C(\C)CCC=C(C)C)C(C)C1=O]

or a pharmaceutically acceptable salt, metabolite, solvate or prodrug thereof.

2. The method of claim 1, where the reducing symptoms of atopic dermatitis comprising an appearance of reduced skin inflammation, a revival of skin physiological function, a revival of skin moisturizing effect, a reduced thickness of epidermis and dermal layers of inflamed skin, or a decreased Eosinophilic leukocytes or Langerhans cells infiltration phenomenon.

3. The method of claim 1, where the compound increases concentration of IFN-γ or IL-12, or decreases concentration of TSLP or total IgE in the subject.

4. The method of claim 1, wherein said cyclohexenone compound, or a pharmaceutically acceptable salt, metabolite, solvate or prodrug thereof, is administered orally, parenterally or intravenously.

5. The method of claim 1, wherein said cyclohexenone compound, or a pharmaceutically acceptable salt, metabolite, solvate or prodrug thereof, is administered by injection.

6. The method of claim 1, wherein said cyclohexenone compound, or a pharmaceutically acceptable salt, metabolite, solvate or prodrug thereof, is administered orally.

7. The method of claim 1, wherein said subject is human.

8. The method of claim 1, wherein said compound is isolated from *Antrodia camphorata*, or prepared synthetically or semisynthetically.

* * * * *